United States Patent
Manassen et al.

(10) Patent No.: US 10,533,940 B2
(45) Date of Patent: *Jan. 14, 2020

(54) SCANNING IN ANGLE-RESOLVED REFLECTOMETRY AND ALGORITHMICALLY ELIMINATING DIFFRACTION FROM OPTICAL METROLOGY

(71) Applicant: KLA-Tencor Corporation, Milpitas, CA (US)

(72) Inventors: Amnon Manassen, Haifa (IL); Andrew V. Hill, Berkley, CA (US); Daniel Kandel, Aseret (IL); Ilan Sela, Haifa (IL); Ohad Bachar, Timrat (IL); Barak Bringoltz, Rishon le Tzion (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,218

(22) Filed: Nov. 12, 2018

(65) Prior Publication Data
US 2019/0094142 A1   Mar. 28, 2019

Related U.S. Application Data

(63) Continuation of application No. 15/841,219, filed on Dec. 13, 2017, now Pat. No. 10,126,238, which is a
(Continued)

(51) Int. Cl.
*G01N 21/55* (2014.01)
*G01N 21/95* (2006.01)
(Continued)

(52) U.S. Cl.
CPC ............. *G01N 21/55* (2013.01); *G01B 11/00* (2013.01); *G01N 21/9501* (2013.01);
(Continued)

(58) Field of Classification Search
CPC .. G01N 21/15; G01N 21/9501; G01N 21/956; G01N 2201/104; G01N 2201/06113; G01B 11/00
See application file for complete search history.

(56) References Cited

U.S. PATENT DOCUMENTS

| 6,023,338 A | 2/2000 | Bareket |
| 6,151,127 A | 11/2000 | Kempe |
(Continued)

FOREIGN PATENT DOCUMENTS

| EP | 1793279 A2 | 6/2007 |
| JP | 2001194323 A | 7/2001 |
(Continued)

OTHER PUBLICATIONS

International Search Report and Written Opinion dated Oct. 16, 2013 for PCT/US2013/047691.
(Continued)

*Primary Examiner* — Sang H Nguyen
(74) *Attorney, Agent, or Firm* — Suiter Swantz pc llo

(57) ABSTRACT

Angle-resolved reflectometers and reflectometry methods are provided, which comprise a coherent light source, an optical system arranged to scan a test pattern using a spot of coherent light from the light source to yield realizations of the light distribution in the collected pupil, wherein the spot covers a part of the test pattern and the scanning is carried out optically or mechanically according to a scanning pattern, and a processing unit arranged to generate a composite image of the collected pupil distribution by combining the pupil images. Metrology systems and methods are provided, which reduce diffraction errors by estimating, quantitatively, a functional dependency of measurement parameters on aperture sizes and deriving, from identified diffraction components of the functional dependency which relate to the
(Continued)

aperture sizes, correction terms for the measurement parameters with respect to the measurement conditions.

20 Claims, 13 Drawing Sheets

Related U.S. Application Data continuation of application No. 14/581,719, filed on Dec. 23, 2014, now Pat. No. 9,958,385, which is a continuation of application No. PCT/US2013/047691, filed on Jun. 25, 2013.

(60) Provisional application No. 61/664,477, filed on Jun. 26, 2012, provisional application No. 61/764,435, filed on Feb. 13, 2013.

(51) Int. Cl.
*G01N 21/956* (2006.01)
*G01B 11/00* (2006.01)

(52) U.S. Cl.
CPC . *G01N 21/956* (2013.01); *G01N 2201/06113* (2013.01); *G01N 2201/104* (2013.01)

(56) References Cited

U.S. PATENT DOCUMENTS

| | | | |
|---|---|---|---|
| 6,512,385 B1 | 1/2003 | Pfaff et al. | |
| 6,633,831 B2 | 10/2003 | Nikoonahad et al. | |
| 6,792,328 B2 | 9/2004 | Laughery et al. | |
| 6,800,859 B1 | 10/2004 | Shishido et al. | |
| 7,081,957 B2 | 7/2006 | Norton | |
| 7,115,858 B1 | 10/2006 | Holden et al. | |
| 7,317,531 B2 | 1/2008 | Mieher et al. | |
| 7,433,034 B1* | 10/2008 | Huang | G01N 21/94 356/237.5 |
| 7,528,941 B2 | 5/2009 | Kandel et al. | |
| 7,528,953 B2 | 5/2009 | Frommer et al. | |
| 7,643,666 B2 | 1/2010 | Setija et al. | |
| 7,884,947 B2 | 2/2011 | De Lega et al. | |
| 7,924,435 B2 | 4/2011 | Colonna De Lega et al. | |
| 8,139,217 B2 | 3/2012 | Van Bilsen et al. | |
| 8,427,634 B2 | 4/2013 | Urano et al. | |
| 8,441,639 B2 | 5/2013 | Kandel et al. | |
| 9,164,397 B2* | 10/2015 | Manassen | G01N 21/55 |
| 2002/0118359 A1 | 8/2002 | Fairley et al. | |
| 2003/0002043 A1* | 1/2003 | Abdulhalim | G03F 7/70633 356/400 |
| 2004/0145744 A1 | 7/2004 | Dobschal et al. | |
| 2004/0146295 A1 | 7/2004 | Furman et al. | |
| 2004/0227944 A1* | 11/2004 | Fukui | G03F 9/7088 356/401 |
| 2005/0057755 A1 | 3/2005 | Johnson et al. | |
| 2005/0123844 A1 | 6/2005 | Monshouwer | |
| 2005/0200850 A1 | 9/2005 | Borden et al. | |
| 2005/0200856 A1* | 9/2005 | Groot | G01B 11/2441 356/512 |
| 2005/0264813 A1 | 12/2005 | Giakos | |
| 2005/0286051 A1 | 12/2005 | Sezginer et al. | |
| 2006/0250609 A1 | 11/2006 | Meeks et al. | |
| 2007/0008533 A1* | 1/2007 | Ghinovker | G03F 7/70633 356/401 |
| 2007/0046953 A1 | 3/2007 | De Groot et al. | |
| 2007/0081170 A1 | 4/2007 | Sezginer et al. | |
| 2008/0117437 A1 | 5/2008 | Vuong et al. | |
| 2008/0151228 A1 | 6/2008 | Hugers | |
| 2008/0293166 A1 | 11/2008 | Sun et al. | |
| 2009/0086184 A1* | 4/2009 | Coston | G03B 27/54 355/67 |
| 2009/0141193 A1 | 6/2009 | Nakayama et al. | |
| 2009/0175530 A1 | 7/2009 | Sjostrom et al. | |
| 2009/0212240 A1 | 8/2009 | Platzgummer et al. | |
| 2009/0225399 A1 | 9/2009 | Zhao et al. | |
| 2009/0310214 A1 | 12/2009 | Brueck et al. | |
| 2010/0010765 A1 | 1/2010 | Li | |
| 2010/0017005 A1* | 1/2010 | Adel | H01L 22/12 700/97 |
| 2010/0128283 A1 | 5/2010 | Liesener et al. | |
| 2010/0295932 A1 | 11/2010 | Yokomachi et al. | |
| 2010/0328655 A1 | 12/2010 | Den Boef | |
| 2011/0069312 A1 | 3/2011 | Kandel et al. | |
| 2011/0075151 A1 | 3/2011 | Jeong | |
| 2011/0109888 A1 | 5/2011 | Van Der Schaar et al. | |
| 2011/0128512 A1* | 6/2011 | Pellemans | G03F 7/70633 355/27 |
| 2011/0228263 A1 | 9/2011 | Chuang et al. | |
| 2011/0261339 A1 | 10/2011 | Van Boxmeer et al. | |
| 2012/0243004 A1 | 9/2012 | El Gawhary et al. | |
| 2012/0327503 A1* | 12/2012 | Manassen | G01J 1/4257 359/291 |
| 2013/0050501 A1 | 2/2013 | Warnaar et al. | |
| 2013/0114085 A1 | 5/2013 | Wang et al. | |
| 2013/0182263 A1 | 7/2013 | Shchegrov et al. | |
| 2014/0065736 A1* | 3/2014 | Amir | H01L 23/544 438/14 |
| 2014/0166862 A1 | 6/2014 | Flock | |

FOREIGN PATENT DOCUMENTS

| | | |
|---|---|---|
| JP | 2010272094 A | 12/2010 |
| JP | 2012083621 A | 4/2012 |
| TW | 200307138 A | 12/2003 |
| TW | 200913023 A | 3/2009 |
| WO | 2004076963 A2 | 9/2004 |
| WO | 2006032485 A1 | 3/2006 |
| WO | 2007103302 A2 | 9/2007 |
| WO | 2007143056 A2 | 12/2007 |
| WO | 2008152802 A1 | 12/2008 |
| WO | 2009127331 A1 | 10/2009 |
| WO | 2011028807 A2 | 3/2011 |
| WO | 2013026598 A1 | 2/2013 |
| WO | 2013124131 A2 | 8/2013 |
| WO | 2013162821 A1 | 10/2013 |
| WO | 2014004564 A1 | 1/2014 |

OTHER PUBLICATIONS

Hester, J. R. et al., "Elimination of Extinction Effects by Extrapolation to Zero Wavelength", Acta Cryst. (1996), A52, 700-704, http://journals.iucr.org/a/issues/1996/05/00/hz0033/hz0033.pdf.

Eeroansky, M., "Extrapolation Method of the Elimination of Instrumental Broadening of Diffraction Lines", Materials Structure, vol. 7, No. 1 (2000), http://www.xray.cz/ms/bul2000-1/ceman.pdf.

* cited by examiner

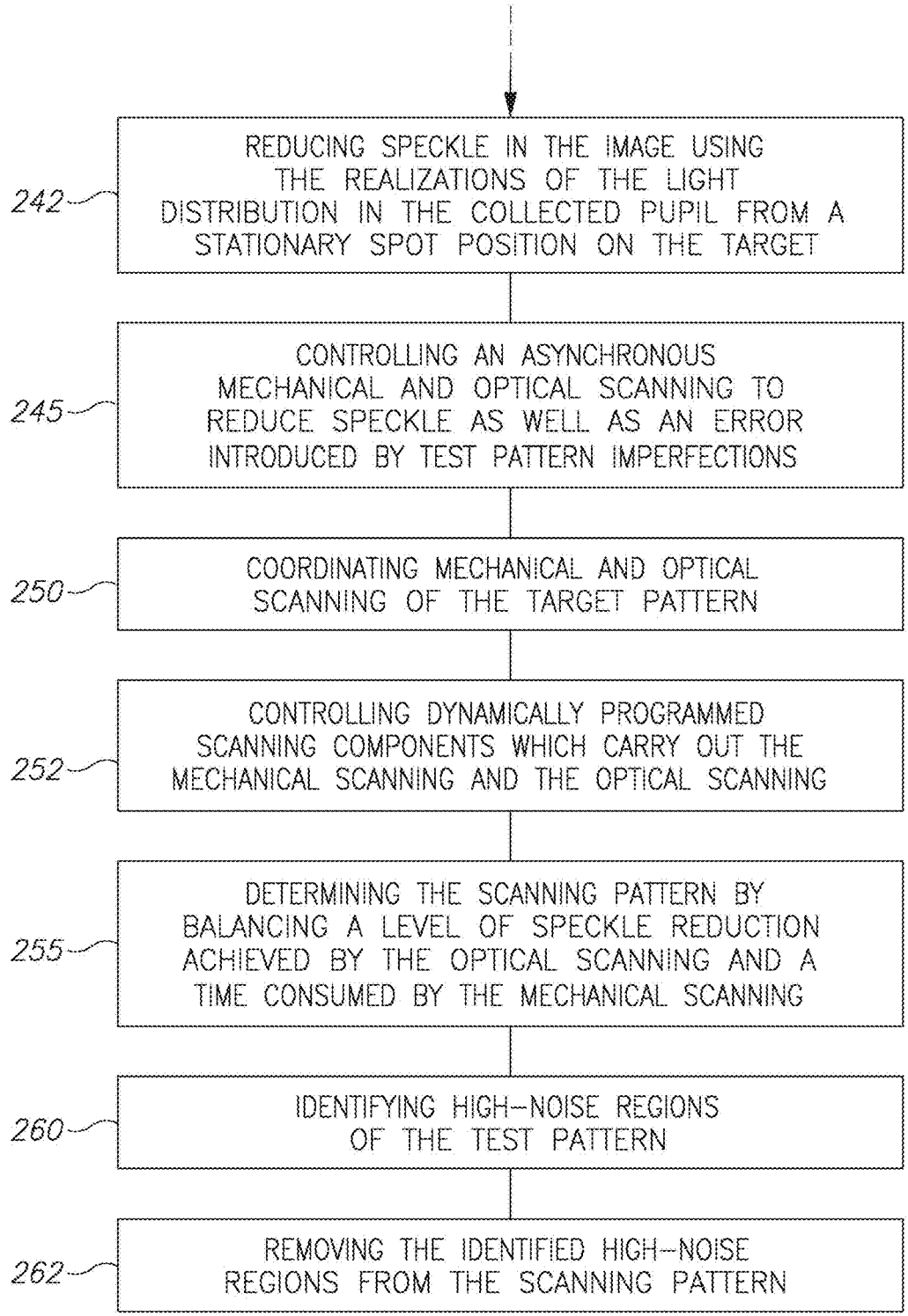
Figure 5 (cont. 1)

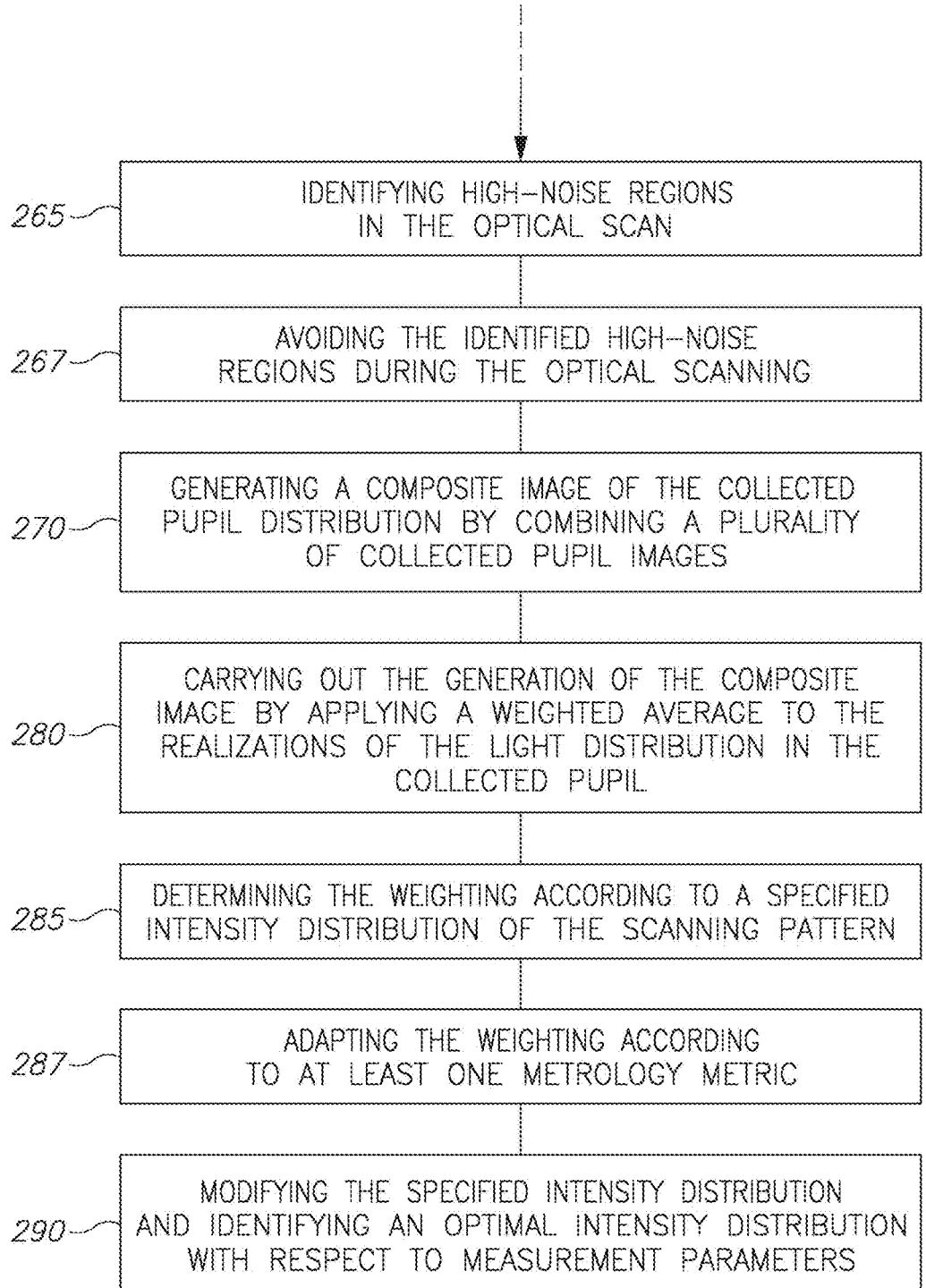
Figure 5 (cont. 2)

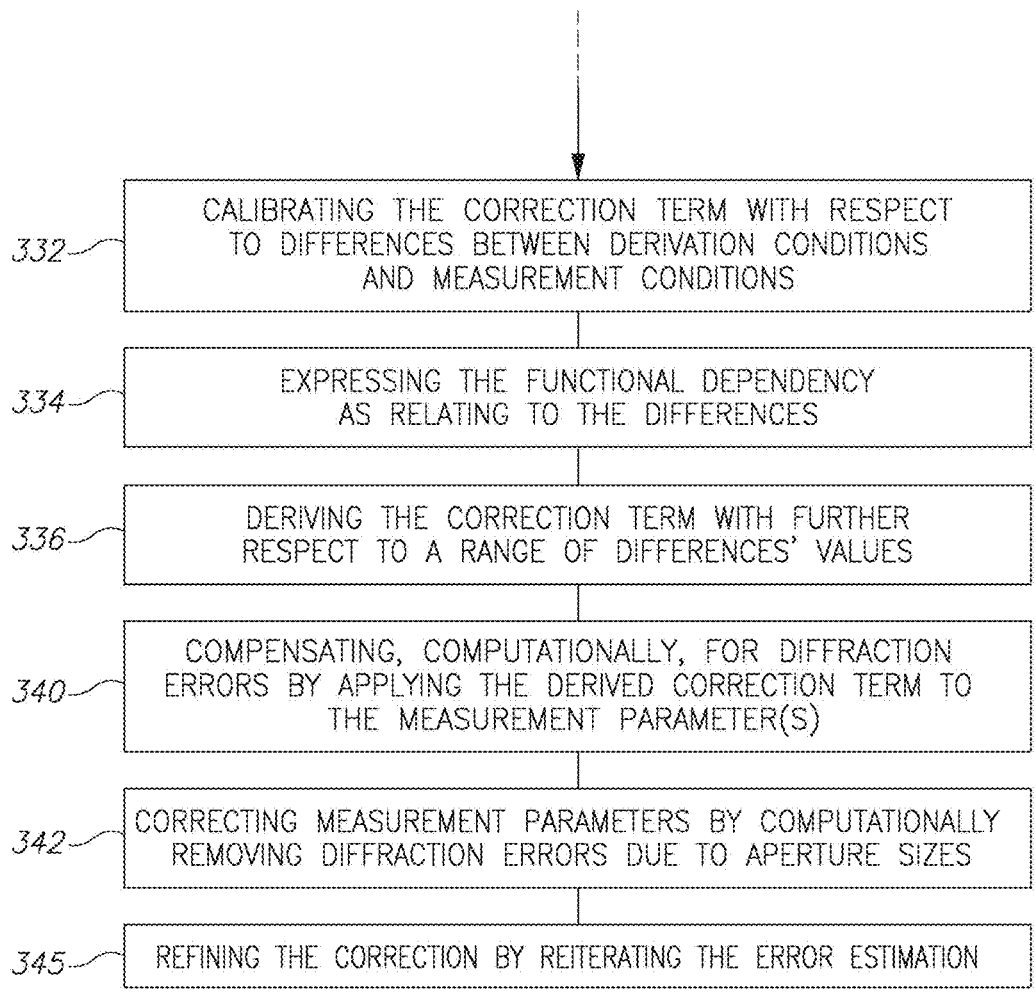
Figure 8 (cont. 1)

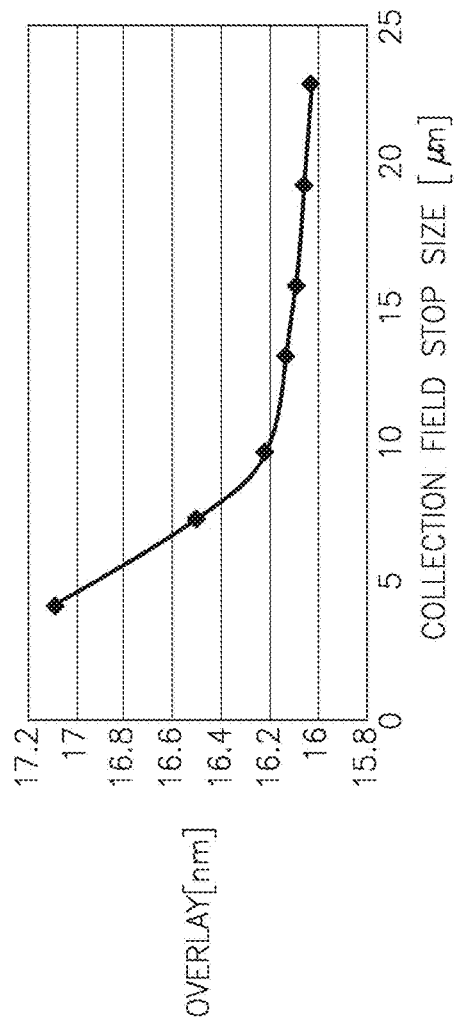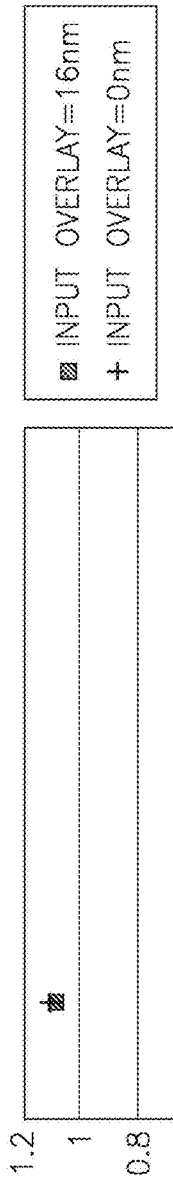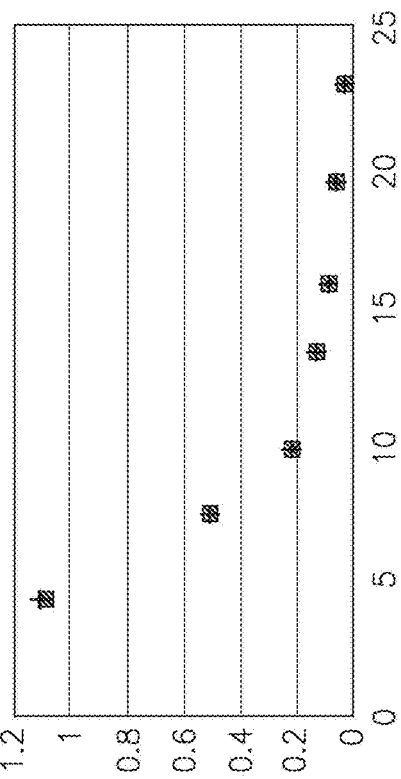
Figure 10A
Figure 10B

SCANNING IN ANGLE-RESOLVED REFLECTOMETRY AND ALGORITHMICALLY ELIMINATING DIFFRACTION FROM OPTICAL METROLOGY

CROSS REFERENCE TO RELATED APPLICATIONS

The present application is related to and claims benefit of the earliest available effective filing date from the following applications. The present application constitutes a continuation patent application of U.S. patent application entitled SCANNING IN ANGLE-RESOLVED REFLECTOMETRY AND ALGORITHMICALLY ELIMINATING DIFFRACTION FROM OPTICAL METROLOGY, naming Amnon Manassen, Andrew Hill, Daniel Kandel, Ilan Sela, Ohad Bachar, and Barak Bringoltz as inventors, filed on Dec. 13, 2017, application Ser. No. 15/841,219, which is a continuation patent application of U.S. patent application entitled SCANNING IN ANGLE-RESOLVED REFLECTOMETRY AND ALGORITHMICALLY ELIMINATING DIFFRACTION FROM OPTICAL METROLOGY, naming Amnon Manassen, Andrew Hill, Daniel Kandel, Ilan Sela, Ohad Bachar, and Barak Bringoltz as inventors, filed on Dec. 23, 2014, application Ser. No. 14/581,719, which is a continuation of International Patent Application Serial No. PCT/US13/47691, filed on Jun. 25, 2013, which claims the benefit under 35 U.S.C. 119(e) of U.S. Provisional Patent Application No. 61/664,477, filed on Jun. 26, 2012 and U.S. Provisional Patent Application No. 61/764,435, filed on Feb. 13, 2013. All of the above-listed applications are incorporated herein by reference in their entirety.

FIELD OF THE INVENTION

The present invention relates to the field of metrology in semiconductor devices and angle-resolved reflectometry, and more particularly, to removal of aperture diffraction effects and to enhancing accuracy and reducing noise in angle-resolved reflectometry.

BACKGROUND OF THE INVENTION

Angle-resolved reflectometry is a technique that is used for measuring parameters such as overlay and critical dimension on a test pattern that is printed on a wafer. A cone of light is focused onto the test pattern and the reflectance of the pattern as a function of angle of incidence is collected in a pupil image. The exact intensity distribution of the light in the collected pupil relative to the intensity distribution in the illumination pupil provides the information necessary to extract precise measurements of the test pattern parameters.

As target sizes become smaller, due to cost and production constraints, applying angle-resolved reflectometry is becoming ever more challenging. The features that make up a test pattern are not uniform throughout the entire test pattern. They invariably contain imperfections such as edge roughness, variable line width and side wall slope inconsistencies. These imperfections in the test pattern features scatter or reflect light in a way that modifies the phase and intensity distribution of the light that is collected by the reflectometer.

Wafer optical metrology tools contain finite size apertures in field planes and in pupil planes. For example, FIG. 6 is a high level schematic illustration of a metrology optical system 90 according to the prior art. FIG. 6 illustrates an optical fiber 91 as light source for inspection of a wafer 80 by a pupil image sensor 94. In this specific schematic example, light travels through an illumination pupil aperture 95A, an illumination filed aperture 95B, an objective pupil aperture 95C and a collection field aperture 95D.

These apertures may or may not be apodized and when placed in the plane reciprocal to the plane where the measurement is made, have the following simple purpose. Light arriving into the detector (be it a detector placed in field plane or a detector placed in pupil plane), contains signals from scattering and diffracting elements that are exterior to the metrology target, and that contaminate the sought for ideal signal. One of the aims of such aperture stops is to block this contaminating light. For example, when the signal is collected in pupil plane, a small aperture placed in a field plane on the collection arm, termed a collection field stop, blocks light from the exterior vicinity of the metrology target.

As the apertures become smaller, the filtering (done in field or in pupil plane) becomes more restrictive and the contaminating light mentioned above is removed in a more efficient way. This, however, comes at the cost of diffractions. Specifically, when the apertures size approaches the spatial coherence length of the radiation, the diffractions off the aperture edges modify the signal in a sizeable amount, and influence the metrology performance. Still, prior art methods suppress diffraction from the field stop by decreasing the spot size (achieved, for example, by means of pupil apodization done in the illumination) and/or choosing the field stop size or shape and a corresponding, judicially chosen region in the collection detector, so that the diffraction effect is small (this may be the case if the larger spot ringing happens on certain areas of the detector).

SUMMARY

One aspect of the present invention provides an angle-resolved reflectometer including a coherent light source, an optical system arranged to scan a test pattern using a spot of coherent light from the light source to yield a plurality of realizations of a light distribution in a collected pupil, wherein the spot covers a part of the test pattern and the scanning is carried out according to a scanning pattern, and a processing unit arranged to generate a composite image of the collected pupil distribution by combining the plurality of realizations of the light distribution in the collected pupil.

One aspect of the present invention provides a method comprising estimating, quantitatively, a functional dependency of at least one measurement parameter on a size of at least one aperture in a metrology system, identifying at least one diffraction component of the functional dependency which relates to the size of the at least one aperture, deriving, from the at least one identified diffraction component, a correction term for the at least one measurement parameter with respect to measurement conditions, the measurement conditions comprising specified sizes of the at least one aperture that generate a diffraction error in the at least one measurement parameter, and compensating, computationally, for the diffraction error by applying the derived correction term to the at least one measurement parameter.

These additional and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 10A is a schematic diagram illustrating an example for the way the inaccuracy in a scatterometry overlay measurement may depend on the size of the collection field stop, according to some embodiments of the invention;

FIG. 10B is a schematic diagram illustrating an example for the way the inaccuracy in a scatterometry overlay measurement depends on the size of the collection field stop for two different values of the true overlay, according to some embodiments of the invention;

DETAILED DESCRIPTION OF THE INVENTION

Figure 2:
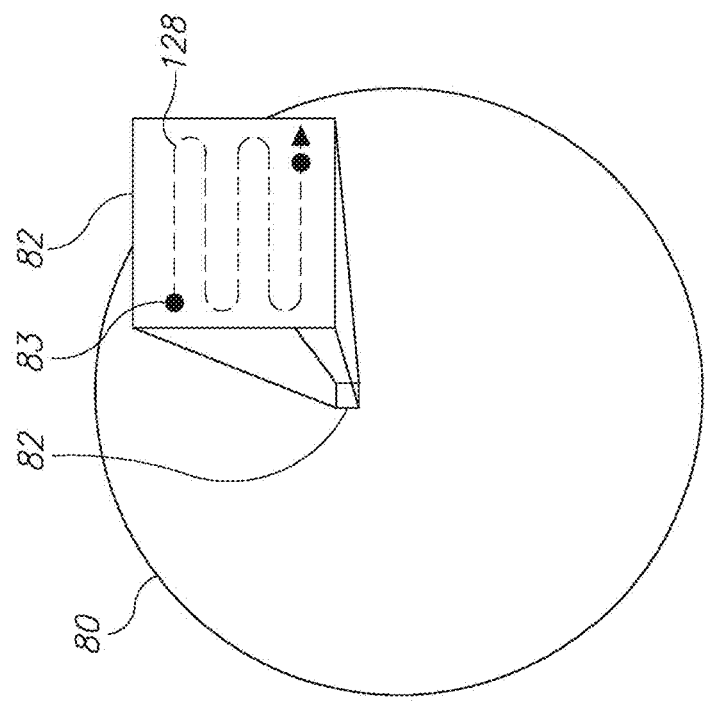
FIG. 2 is a high level schematic diagram illustrating an angle-resolved reflectometer implementing a scanning pattern, according to some embodiments of the invention.

Prior to setting forth the detailed description, it may be helpful to set forth definitions of certain terms that will be used hereinafter.

The terms "target" or "metrology target" as used herein in this application refer to any structure that is used for metrology needs. Targets may be part of any layer in the lithographic process, and targets may include different structures on the same layer or on different layers.

The terms "speckle pattern" or "speckle" as used herein in this application refer to an intensity pattern of an optical signal that is produced by interference of at least two wavefronts, and generally to a source of measurement error resulting from interfering wavefronts at the sensor plane.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1:
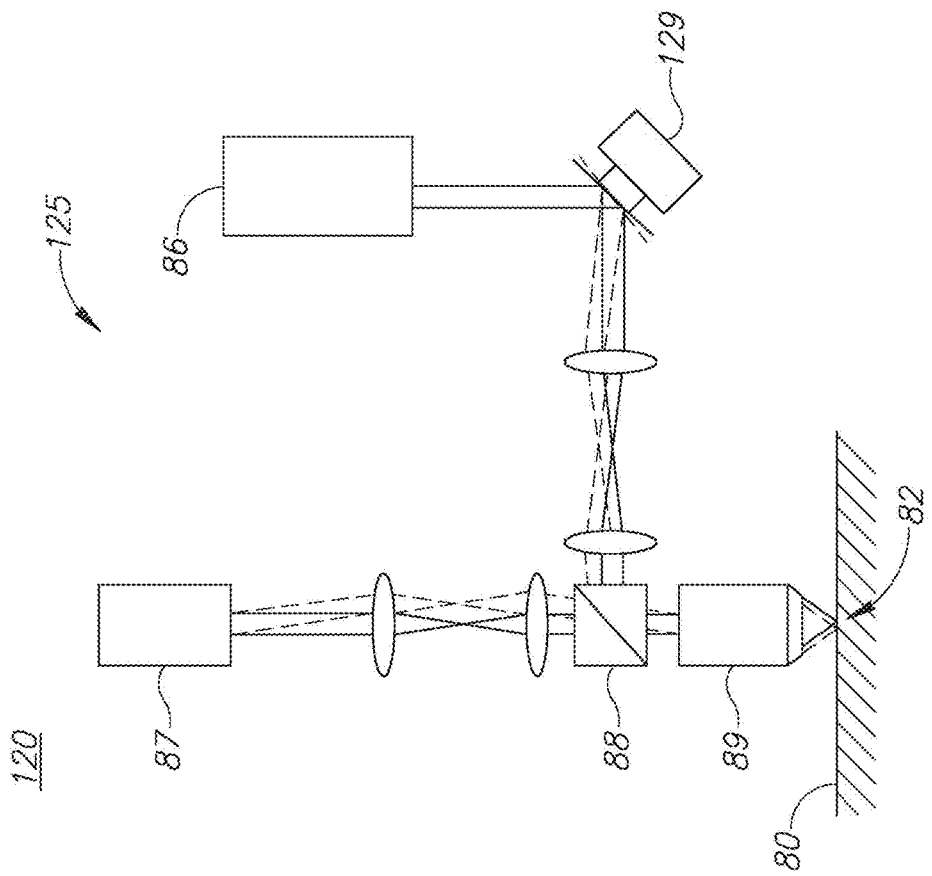
FIG. 1 is a high level schematic diagram illustrating an angle-resolved reflectometer with optical scanning, according to some embodiments of the invention.

FIG. 1 is a high level schematic diagram illustrating an angle-resolved reflectometer 120 with optical scanning, according to some embodiments of the invention. FIG. 2 is a high level schematic diagram illustrating angle-resolved reflectometer 120 implementing a scanning pattern 128, according to some embodiments of the invention.

Embodiments of the invention comprise an angle-resolved reflectometer 120 comprising a coherent light source 86 and an optical system 125 arranged to scan a test pattern 82 using a spot 83 of coherent light from light source 86 to yield, at detector 87, a plurality of realizations (i.e. pupil images) of the light distribution in the collected pupil. In an example embodiment, differences between the realizations of the light distribution in the collected pupil are a consequence of speckle and noise, which may be identified and removed by comparing the realizations. Spot 83 covers a part of test pattern 82 and the scanning is carried out according to a scanning pattern 128 (see below, FIG. 3). The scanning may be carried out mechanically, by moving test pattern 82 with respect to an objective lens 89 of optical system 125 (e.g. by moving objective lens 89 with respect to a wafer 80 having target 82 or by moving wafer 80 with respect to objective lens 89), or the scanning may be carried out optically by changing the beam path of the illuminating spot (see below). Reflectometer 120 further comprises a processing unit 130 arranged to generate a composite image of the collected pupil distribution by combining the plurality of realizations (i.e. pupil images) of the light distribution in the collected pupil. For example, the collected pupil may be the pupil of objective lens 89.

In an example embodiment, reflectometer 120 focuses spatially coherent illumination on a smaller spot than is achievable using spatially incoherent illumination. Angle-resolved reflectometer 120 may be able, by utilizing spatially coherent illumination, to support smaller test patterns compared with a reflectometer 120 using spatially incoherent illumination. Coherent light source 86 may comprise a laser source that is capable of generating bright spatially coherent illumination that provides sufficient illumination for angle-resolved reflectometer 120. Such illumination avoids high levels of shot noise which result from insufficient brightness of spatially incoherent light sources.

Figure 3:
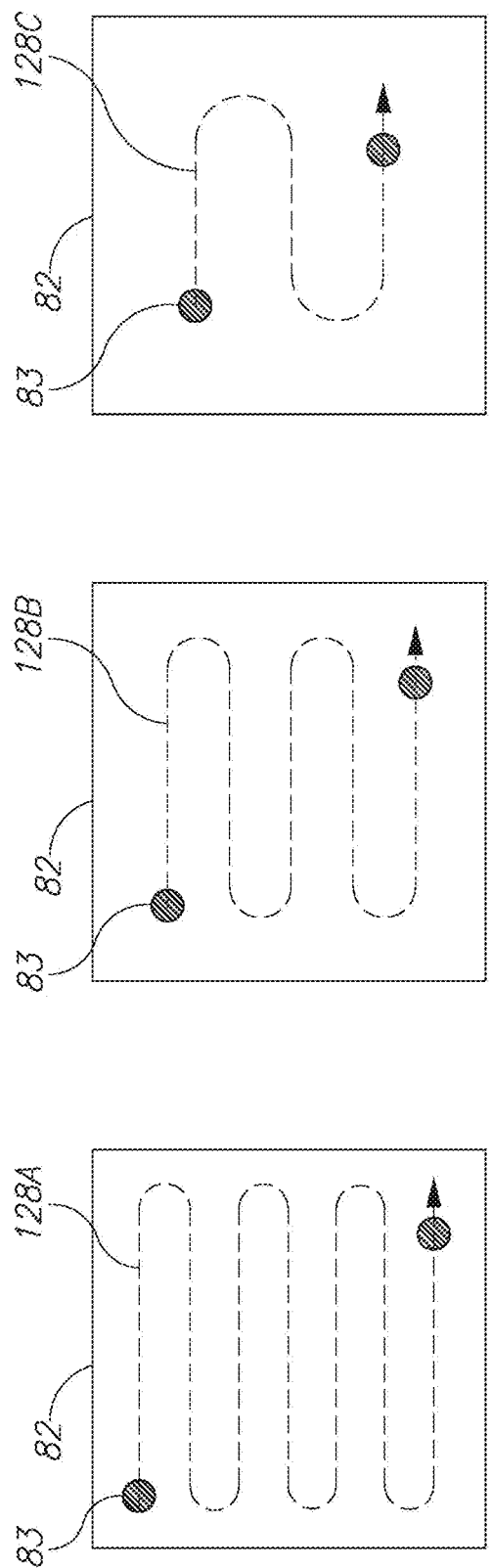
FIG. 3 is a high level schematic diagram illustrating scanning patterns having different sizes and densities, according to some embodiments of the invention.

FIG. 3 is a high level schematic diagram illustrating scanning patterns 128 having different sizes and densities, according to some embodiments of the invention. For example, to the left, FIG. 3 illustrates a scanning pattern 128A which is relatively dense and yields relatively low noise but takes the longest measurement time. To the right, FIG. 3 illustrates a scanning pattern 128C which is relatively sparse and small and yields relatively high noise yet takes the shortest measurement time. Scanning pattern 128B is intermediate between 128A and 128C with respect to its size, level of noise and scanning duration.

In an example embodiment, the parameters of scanning pattern 128 and spot 83 may be configured to optimize the measured parameters and reduce errors arising from imperfections in test pattern features. Adjusting the parameters of scanning pattern 128 and spot 83 may be carried out before operation as a calibration procedure, or during measurements as a dynamic measurement procedure.

The impact of such errors may be reduced by illuminating larger areas, with a larger spot 83, of test pattern 82 and capturing the reflected light from this larger area. In this way the impacts of imperfections in target 82 are reduced through averaging. While using the spatially coherent illumination results in illuminating only relatively small spots 83 on test pattern 82, moving wafer 80 relative to the focused spot 83 allows a larger area of test pattern 82 to be illuminated. The wafer scan may be carried out during the time it takes for the system sensor to capture one image of the light distribution in the pupil or successive images can be captured as different areas of the target 82 are illuminated. When successive images are captured, they can be combined to represent an average image of the light distribution in the pupil. Translating wafer 80 to move spot 83 on target 82 is one possible implementation. A similar implementation would consist of translating objective lens 89 relative to target 82 and wafer 80 so that the focused spot 83 translates on test pattern 82.

FIG. 1 illustrates an embodiment in which the scanning is carried out optically rather than mechanically (i.e. without physical relative movement of lens 89 and target 82). In this example, the optical scanning may be carried out by tilting a tiltable mirror 129 (as a non-limiting example of an optical scanning) in optical system 125, and thereby reduce speckle error in the optical path, as explained in the following.

When a spatially coherent beam propagates through optical system 125, light scattered by imperfections in the optical components propagates with the original beam (from light source 86) as additional coherent wavefronts. At a sensor plane (of detector 87), the original beam interferes with the scattered wavefronts to generate speckle in the image. A small change in the position or pointing of the original beam can change the relative positions and angles of scattered wavefronts sufficiently so that the resulting speckle pattern is wholly or partially decorrelated with the original speckle pattern. This same motion in the original beam may be sufficiently small that its character at the detector 87 is essentially unchanged. Without wishing to be bound by theory, when many speckle patterns are generated within the acquisition time of detector 87, the magnitude of the residual speckle in the image is reduced through the averaging of the many decorrelated speckle patterns. It would also be possible to acquire a succession of images each with a different beam orientation and decorrelated speckle pattern. These successive images may be averaged with the resulting effect of reducing the magnitude of the residual speckle in the image. Changing the position of the spatially coherent beam over time and summing the resulting images has the general effect of decreasing the spatial coherence of the image.

In an example embodiment, the position and angle of a spatially coherent beam may be modified using scanning optical component 129 such as a piezo driven scan mirror, resonant scanner, rotating polygon scanner, spinning holographic scanner or acousto-optic deflector. Reflectometer 120 may controllably scan the spatially coherent beam so that it moves about a pupil plane, scan the beam so that it moves about a field plane or scan the beam so that it moves about in both the pupil and field planes. In angle-resolved reflectometer 120, it is critical to have a stable, low-noise beam distribution in the pupil plane. For this reason, a motion that leaves the beam position essentially stationary in the pupil plane and scans the beam position in the field plane is a preferred implementation.

Figure 4:
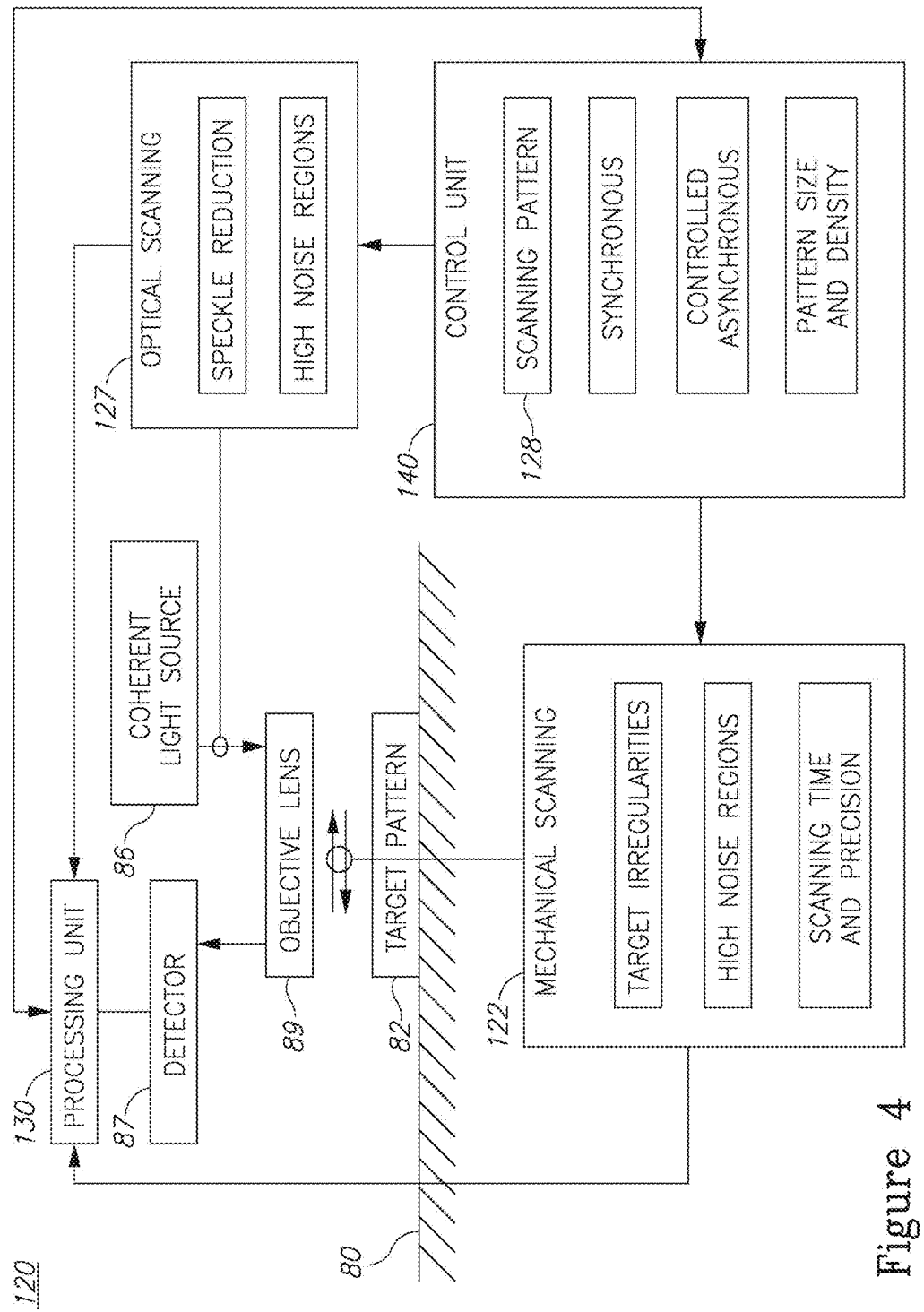
FIG. 4 is a high level schematic block diagram illustrating various parameters and controlled variables of a scanning angle-resolved reflectometer, according to some embodiments of the invention.

FIG. 4 is a high level schematic block diagram illustrating various parameters and controlled variables of scanning angle-resolved reflectometer 120, according to some embodiments of the invention. FIG. 4 schematically illustrates coherent light source 86, detector 87 and objective lens 89 of reflectometer 120, as well as parameters and characteristics associated with mechanical scanning 122 (relative translational movement of objective lens 89 and wafer 80 with target 82) and optical scanning 127, as explained below. Reflectometer 120 may comprise a control unit 140 arranged to control scanning pattern 128 (as explained above and below) and control and coordinate mechanical and optical scanning 122, 127 and the interrelation between them, as explained below. Reflectometer 120 may comprise a processing unit 130 arranged to process images from detector 87, generate measurements and integrate images from the processed images and further provide feedback to control unit 140 regarding different features of the images, as these are taken and processed. As explained below, such feedback allows further noise reduction by additional manipulation of either or both mechanical and optical scanning 122, 127.

In an example embodiment, scanning target 82 may be carried out by synchronous optical and wafer (mechanical) scanning to yield multiple realizations of the light distribution in the collected pupil from a stationary spot 83 on target 82. The realizations may differ from each other in the speckle they possess, which may thus be removed. Processing unit 130 may be further arranged to reduce speckle in the image using the realizations of the light distribution in the collected pupil from a stationary spot position. Scanning the beam through optical system 125 may be utilized to reduce the speckle in the final pupil image by generating and averaging many decorrelated speckle images, but at the same time focused spot 83 scans over a larger area of test pattern 82. This has the potentially negative effect of requiring a larger test pattern 82 which consumes more valuable area on wafer 80. By combining optical scanning 127 and mechanical scanning 122, reflectometer 120 may be configured to reduce speckle in the image and spot 83 may be kept stationary on test pattern 82 by precisely synchronizing mechanical scan 122 and optical scan 127 by control unit 140.

In an example embodiment, scanning target 82 may be carried out by controllably asynchronous mechanical and optical scanning 122, 127. Processing unit 130 may be further arranged to reduce speckle in the image using optical scanning 127 and to reduce an error introduced by test pattern imperfections using mechanical scanning 122. While optical scans 127 and wafer scans 122 can be synchronized in angle-resolved reflectometer 120 to scan the spatially coherent beam through optical system 125 and keep it stationary on test pattern 82, the scans may also be intentionally desynchronized. Such controllable desynchronization may be used to allow for the beam to be scanned through optical system 125 to reduce the magnitude of the speckle that is introduced in the image while also controlling the size of the region of test pattern 82 that is illuminated to minimize the impact of test pattern imperfections. The magnitude of optical scan 127 may be set to achieve the desired speckle reduction, and the magnitude of mechanical scan 122 desynchronization may be set to achieve the desired averaging over test pattern 82 imperfections.

In an example embodiment, control unit 140 may be further arranged to determine scanning pattern 128 by balancing a level of speckle reduction achieved by optical scanning 127 and a time consumed by mechanical scanning 122. In particular, scanning pattern 128 may be optimized to balance noise reduction and measurement time. For a given test pattern 82, reflectometer 120 may be arranged to minimize the impacts of feature imperfections by scanning over the largest possible area and the most possible points within the area. Reflectometer 120 may also be arranged to achieve the greatest optical speckle reduction by scanning the largest possible range within optical system 125 and by scanning over the most possible points within the scan range. However, large and dense scanning patterns 128A (e.g. FIG. 3, to the left) that originate either from translating wafer 80 or from optical scanning 127 (e.g. by optical component 129) may require a relatively long time to execute. It is desirable for semiconductor metrology tools to take as little time as possible to make measurements. Short measurement times increase a tools wafer throughput and lowers its cost of ownership. A direct tradeoff exists between scan range and density and measurement time.

In an example embodiment, reflectometer 120 may comprise dynamically programmed scanning components for performing mechanical scanning 122 and optical scanning 127. Control unit 140 may be arranged to control the dynamically programmed scanning components to optimize noise, error and speckle reduction with operational parameters such as measurement duration and accuracy.

Examples for dynamically programmable scanning components comprise wafer stages and tilt mirrors. These may be dynamically programmed to set their scanning ranges and patterns. This provides the option to modify a particular system's balance between noise reduction, via scan range and density, and measurement speed. Reflectometer 120 may thus be configured for a short scan that produces lower precision results but at a faster wafer throughput (e.g., akin to scanning pattern 128C) and then be modified for a long scan that produces higher precision results at a slower wafer throughput (e.g., as illustrated by scanning pattern 128A). Overall scanning patterns 128A-C ranges of measurement precision and measurement durations, which may be dynamically controlled by control unit 140.

In an example embodiment, reflectometer 120 may implement and utilize programmed scanning patterns 128 for intelligent reduction of test pattern and optical noise. For example, there may be instances in which particular areas of test pattern 82 introduce more measurement noise than other areas. In an example embodiment, processing unit 130 of reflectometer 120 may be arranged to identify high-noise regions of test pattern 82. In an example embodiment, control unit 140 of reflectometer 120 may be arranged to remove the identified high-noise regions from test pattern 82. In another example, particular areas within optical scanning pattern 128 might introduce more noise than other areas within the optical scan 127. In an example embodiment, processing unit 130 of reflectometer 120 may be arranged to identify high-noise regions in optical scan 127. In an example embodiment, control unit 140 of reflectometer 120 may be arranged to avoid the identified high-noise regions during optical scanning 127.

In an example embodiment, reflectometer 120 may be arranged to identify these high-noise regions of test pattern 82 and optical scan 127 during a training mode. Test scanning pattern 128, mechanical scanning 122 and/or optical scanning 127 may then be defined to avoid these high-noise areas during actual measurements. This principle could be applied to only mechanical scan 122, only optical scan 127, or to a combination of mechanical and optical scans 122, 127.

In an example embodiment, scanning pattern 128 may further comprise a specified intensity distribution as a function of scan positions. The specified intensity distribution may be implemented in mechanical scanning 122 and/or optical scanning 127. For example, the specified intensity distribution may be symmetric but non-uniform, such as a Gaussian distribution. The specified intensity distribution may comprise a shape function of scanning pattern 128 (e.g. circular, rectangular etc.) and/or a profile function (e.g. Gaussian or any other symmetric distribution) of scanning pattern 128. The intensity distribution may be used to increase metrology accuracy, with or without relation to the identification of high noise regions described above.

In an example embodiment, processing unit 130 may be further arranged to carry out the generation of the composite image by applying a weighted average to the realizations of the light distribution in the collected pupil, each realization reflecting a different optical and/or mechanical scan position. The weighting may be determined according to the specified intensity distribution of scanning pattern 128, for example the weighting may enhance any part of the intensity distribution. Hence, the individual metrology results obtained per scan point may be combined into an analysis which, while not being a simple intensity average over collection pupil configurations, yields a more accurate and repeatable metrology result. The weighted average and the weighting parameters may be selected to optimize the metrology results.

In an example embodiment, processing unit 130 may be further arranged to adapt the weighting according to at least one metrology metric, such as metrology sensitivity to the position of spot 83.

In an example embodiment, control unit 140 may be arranged to control or modify the specified intensity distribution of scanning pattern 128 to identify or optimize the intensity distribution (shape and function) to a specific test pattern 82, to specific measurement stacks or according to metrology configurations. For example, different intensity distributions may be applied in train mode and measurement results of processing unit 130 may be compared to identify an optimal intensity distribution of spot 83.

Figure 5:
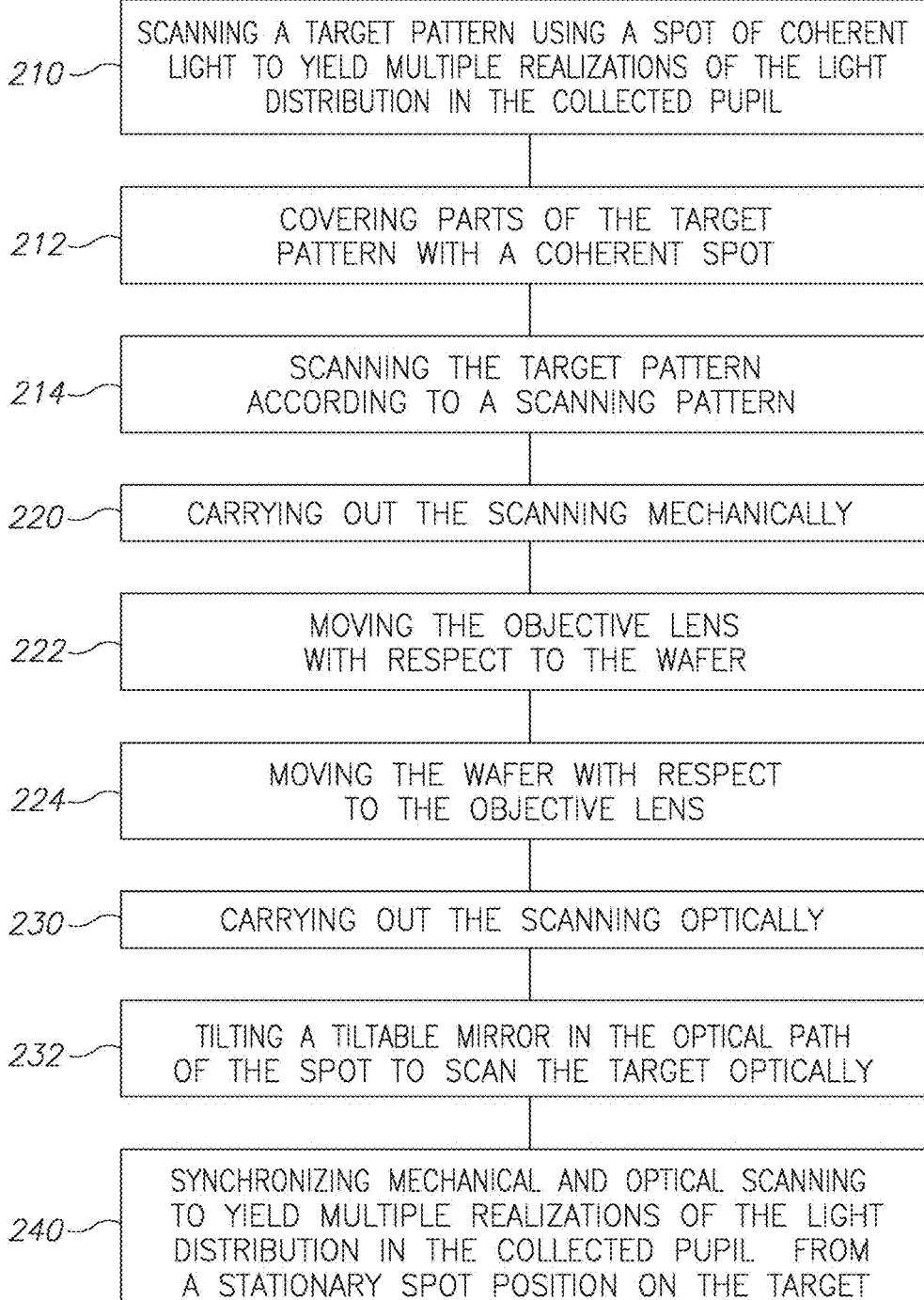
FIG. 5 is a high level schematic flowchart illustrating an angle-resolved reflectometry method, according to some embodiments of the invention.

FIG. 5 is a high level schematic flowchart illustrating an angle-resolved reflectometry method 200, according to some embodiments of the invention. Method 200 comprises scanning a test pattern using a spot of coherent light to yield a plurality of realizations of a light distribution in a collected pupil (stage 210) and generating a composite image of the collected pupil distribution by combining a plurality of collected pupil images (stage 270). In an example embodiment, scanning 210 may comprise covering parts of the test pattern with a coherent spot (stage 212) and/or scanning the test pattern according to a scanning pattern (stage 214).

In an example embodiment, method 200 may comprise carrying out the scanning mechanically (stage 220), e.g., by moving the objective lens with respect to the wafer (stage 222) or by moving the wafer with respect to the objective lens (stage 224)).

In an example embodiment, method 200 may comprise carrying out the scanning optically (stage 230) (e.g., by tilting a tiltable mirror in the optical path of the spot to scan the target optically (stage 232)).

In an example embodiment, method 200 may comprise synchronizing mechanical and optical scanning to yield multiple realizations of the light distribution in the collected pupil from a stationary spot position on the target (stage 240) and reducing speckle in the image using the realizations of the light distribution in the collected pupil from the stationary spot positions (stage 242). Alternatively or complementarily, method 200 may comprise controlling an asynchronous mechanical and optical scanning to reduce speckle as well as an error introduced by test pattern imperfections (stage 245).

Generally, method 200 may comprise coordinating mechanical and optical scanning of the test pattern (stage 250), e.g. by controlling dynamically programmed scanning components which carry out the mechanical scanning and the optical scanning (stage 252).

In an example embodiment, method 200 may comprise determining the scanning pattern by balancing a level of speckle reduction achieved by the optical scanning and a time consumed by the mechanical scanning (stage 255). In other embodiments, method 200 may comprise identifying high-noise regions of the test pattern (stage 260) and removing the identified high-noise regions from the scanning pattern (stage 262), and/or identifying high-noise regions in the optical scan (stage 265) and avoiding the identified high-noise regions during the optical scanning (stage 267).

In an example embodiment, the spot of coherent light has a specified intensity distribution and method 200 may further comprise carrying out the generation of the composite image by applying a weighted average to the realizations of the light distribution in the collected pupil (stage 280). The weighting may be determined according to the specified intensity distribution of the scanning pattern (stage 285). In an example embodiment, method 200 may further comprise adapting the weighting according to at least one metrology metric (stage 287). In an example embodiment, method 200 may further comprise modifying the specified intensity distribution and identifying an optimal intensity distribution with respect to measurement parameters such as a specific test pattern or metrology configuration (stage 290).

Advantageously, reflectometers 120 and methods 200 may provide any of the following multiple benefits: (i) reflectometer 120 and method 200 may enable smaller test patterns 82 because spatially coherent illumination may be focused to a smaller spot 83 than spatially incoherent illumination; (ii) reflectometer 120 and method 200 may reduce impacts of test pattern 82 imperfections because scanning the wafer 80 relative to the illumination spot 83 during the image acquisition reduces the impacts of test pattern 82 imperfections through averaging; (iii) reflectometer 120 and method 200 may reduce impacts of optical noise because scanning the beam through the optics reduces the impacts of speckle noise by averaging many decorrelated speckle views during the image acquisition; (iv) reflectometer 120 and method 200 may enable reduction of optical noise on small test patterns 82 because synchronizing wafer stage motion with optical scan motion may allow the optical beam to be scanned through the optics for speckle reduction while keeping the spot 83 stationary on the small test pattern 82; (v) reflectometer 120 and method 200 may enable the optimization of optical noise reduction and test pattern 82 noise reduction because desynchronizing wafer 80 stage motion and optical scan motion may allow any optical beam scan through the optics for speckle reduction and any spot 83 scan on the target for target noise reduction; (vi) reflectometer 120 and method 200 may enable optimization of noise reduction and measurement speed because the size and density of the optical and wafer scans can be modified to tradeoff between noise reduction and measurement speed; (vii) reflectometer 120 and method 200 may enable avoidance of high-noise region of test pattern 82 and optics because the scanned areas of the test pattern 82 and optics may be defined to avoid regions which introduce high levels of measurement noise; and (viii) reflectometer 120 and method 200 may maximize test pattern noise reduction because incoherent illumination at the exit of a multimode fiber uniformly illuminates the intended area of the test pattern 82.

These benefits may be achieved by various configurations of reflectometer 120 and method 200, which may incorporate any subgroup of features from those described above. Embodiments of reflectometer 120 and method 200 may combine any of the following features: (i) illumination of the sample with substantially spatially coherent illumination; (ii) use of stage scanning during the acquisition of a measurement of a single test pattern 82; (iii) use of optical scanning during the acquisition of a measurement of a single test pattern 82; (iv) combination of stage scanning and optical scanning during the acquisition of a measurement of a single test pattern; (v) stage scanning synchronized with optical scanning so that the illumination spot is kept stationary on the test pattern 82 during the acquisition of the measurement from this test pattern 82; (vi) stage scanning desynchronized in a controlled manner with optical scanning so that independent scan patterns can be generated in the beam passing through the optics and in the spot motion on the test pattern during the acquisition of a measurement of a single test pattern 82; and (vii) an ability to adjust scan size and density for optimizing the tradeoff between measurement noise and measurement time during the acquisition of the measurement of a single test pattern 82; and (viii) reduction of spatial coherence by scanning a laser spot at the entrance of a multimode fiber.

Advantageously, reflectometers 120 and methods 200 overcome the following limitations of current technologies.

Since wafers 80 are expensive to process, as much of the wafer 80 area as possible needs to be reserved for functional circuitry. To this end, it is desirable to make test patterns 82 small so that they consume little wafer 80 area. To avoid interaction between the measurement light and wafer 80 geometries surrounding the test pattern 82, the size of the focused spot 83 in an angle-resolved reflectometer 120 must be even smaller than the test pattern 82. The smallest possible spot 83 can be formed by focusing a spatially coherent beam of light. An angle-resolved reflectometer that focuses a spatially coherent beam onto the test pattern 82 has a potential competitive advantage over reflectometers that use less spatially coherent light, in that the smaller focused spot 83 can allow for smaller test patterns 82 and leave more wafer 80 area available for functional circuitry.

When measurements of the test pattern 82 are made with a small focused spot 83 the magnitude of these modifications to the light distribution can lead to significant errors or noise in the measurement of the test pattern parameters. An angle-resolved reflectometer 120 that is capable of collecting information from as much of the test pattern 82 as possible has a competitive advantage in that the measurement error introduced by target imperfections can be minimized through spatial averaging.

When a spatially coherent beam propagates through an optical system 125, imperfections in the optical components scatter some fraction of the beam. This scattered light propagates along with the primary beam and interferes with it to produce speckle. In an optical metrology system, such as an angle-resolved reflectometer 120, information regarding a test pattern 82 is contained in the reflected intensity profile of the spatially coherent beam. Speckle created by the optical system 125 can modulate the beam intensity in an unpredictable manner and result in errors in the subsequent measurement of test pattern 82 parameters.

The disclosed reflectometers 120 and methods 200 are capable of minimizing the size of the illuminated area on the wafer 80 to support the smallest possible test patterns 82, as well as illuminating as large of an area of the test pattern 82 as necessary to minimize the impacts of pattern imperfections, while concurrently minimizing the measurement errors introduced by speckle generated in the optical system 125.

Advantageously, reflectometers 120 and methods 200 provide better solutions than technologies related to stationary spatially incoherent illumination and stationary spatially coherent illumination.

In stationary spatially incoherent illumination, the size of the spot of spatially incoherent light that is focused onto the wafer can be defined by a field stop placed in the illumination path of the optical system. By increasing the size of the field stop the area of the test pattern that is illuminated can be increased and the impacts of target imperfections can be reduced by effectively averaging the measurement over a larger area of the test pattern. Limitations to a configuration utilizing spatially incoherent illumination arise when the size of the test pattern needs to be decreased. Decreasing the size of the test pattern requires a reduction in the size of the illuminated spot as well. This can be accomplished by reducing the size of the field stop, but this results in a significant loss of light and an increase in spatial coherence. An angle-resolved reflectometer that uses a spatially incoherent light source is thus light starved when illuminating small test patterns. The loss of additional light at the field stop worsens the situation and increases measurement errors due to shot noise. Increasing the spatial coherence by decreasing the size of the field stop increases the impacts of speckle from the optical system as well. An angle-resolved reflectometer with stationary spatially incoherent illumination is hence not optimal for measuring small test patterns, because it suffers from increasing shot noise and speckle as the illumination field stop is decreased to support the smaller test patterns.

In stationary spatially coherent illumination, a spatially coherent beam can be focused to a small spot on the wafer and this allows for the test pattern to be made small as well. However, the small spot illuminates local imperfections in the test pattern and does not reduce the impacts of these imperfections by averaging over a larger area of the test pattern. Spatially coherent illumination also generates speckle in the optical system which adds noise to the test pattern measurements. An angle-resolved reflectometer with stationary spatially coherent illumination can measure small test patterns, but cannot be adjusted to increase the size of the illuminated patch to allow for averaging of test pattern imperfections and suffers from speckle noise.

Hence, reflectometers 120 and methods 200 are superior to these two approaches.

In an example embodiment, method 200 may be used to implement spatial coherence reduction in multimode fibers. For example, embodiments of the invention may comprise scanning a face of a multimode fiber using a spot of coherent light to yield a signal having reduced spatial coherence yield mix modes.

A large-core multimode fiber may be used to deliver spatially coherent light to the measurement head. The multimode fiber acts like an extended object if different points on the fiber face are uncorrelated. Ordinarily, a laser coupled into a multimode fiber only excites a small subset of modes of the fiber. To achieve the desired decorrelation, the laser may be arranged to excite all, or a broad distribution of, the modes of the fiber. Randomness is not necessary for decorrelation. Decorrelation may be achieved by exciting the modes sequentially on a time scale long compared to the coherence time. Then the short correlation time is transferred to a short correlation length. Randomness just adds noise. Unfortunately, fiber instability will always generate some randomness. The point of adding additional randomness is that lots of randomness can be quieter than a little randomness.

An approach for achieving this may be to laterally scan the focused laser beam across the fiber face, or to laterally scan the fiber face across the focused laser beam, in a random or pseudo-random pattern. Such scanning is akin to scanning pattern 128 that was illustrated above and may likewise be carried out optically or mechanically. This scan may be carried out e.g. using a fold mirror with a high speed tip-tilt actuator. If the scan is sufficiently fast, the time-varying mode structure is averaged out over the integration time of the detector 87, resulting in essentially an incoherent extended source. Another approach for randomly mixing the modes would be to vibrate the multimode fiber using a voice coil or other actuator.

When performing wafer metrology, accuracy, precision, and tool induced shift (TIS) depend on the capacity to retrieve high fidelity spectroscopic or angular information from small metrology targets. Good metrology performance requires a method for weeding out the induced diffractions from the apertures discussed above. The present invention teaches extrapolating the diffraction-induced signal contamination that reduces the performance of prior art measurements to a "no-diffraction" limit where the metrology performance is clean of such diffraction effects.

Diffraction through apertures in a metrology system introduces errors which are distinguishable in the measurement output. Embodiments of the invention compensate for these errors computationally by deriving a functional dependency of at least a part of the error on the aperture size. The functional dependency may be derived for different measurement parameters, such as metrology results or measured intensities. The derivation may be carried out before actual measurements or during the measurements (on the fly). The functional dependency may be used to calibrate the measurement system for a large set of aperture size combinations with respect to multiple apertures in the system.

Figure 6:
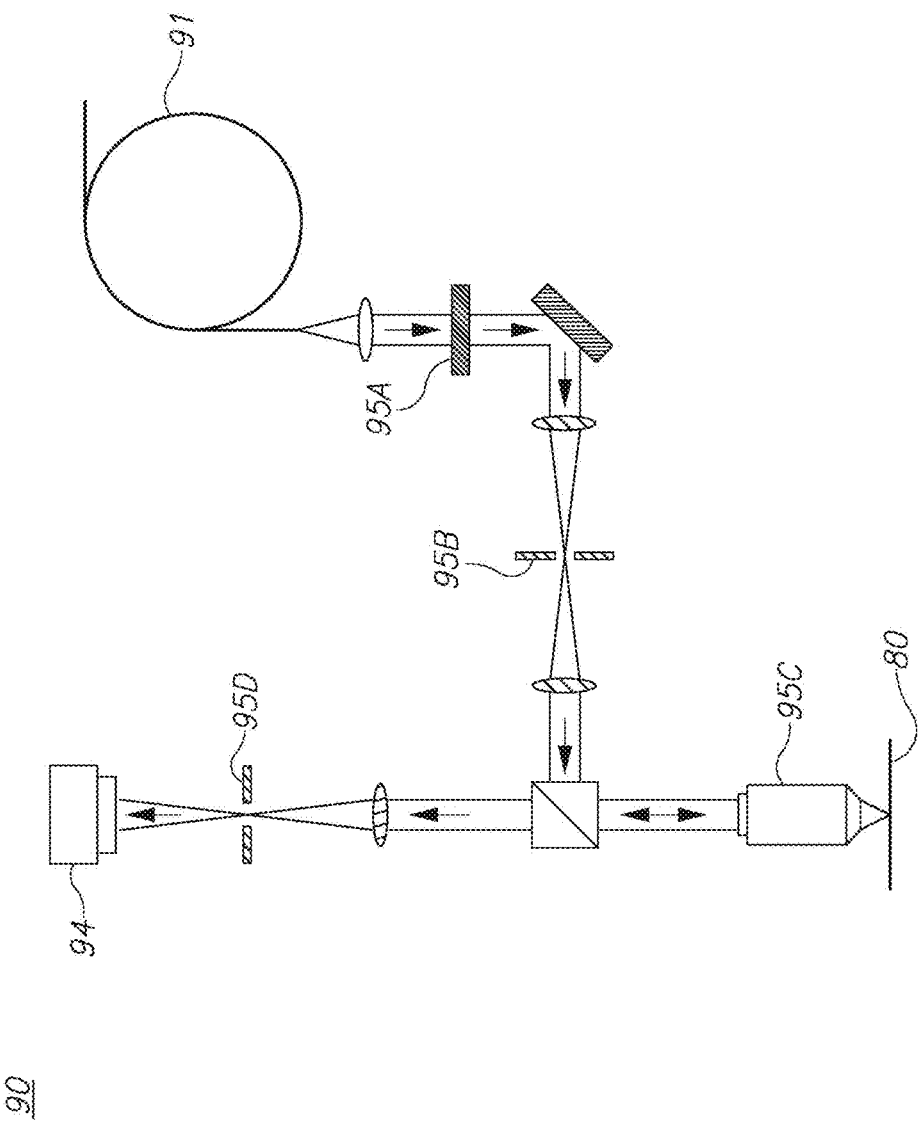
FIG. 6 is a high level schematic illustration of a metrology optical system according the prior art.

Disclosed methods also provide the margin of error of the measurement induced by the diffraction related signal contamination. As illustrated in FIG. 6, various apertures in metrology optical system 90 may induce diffraction errors.

Diffraction effects may cause a degradation of metrology performances such as accuracy and may also cause a degradation of precision due to an enhanced sensitivity to focus and radiation spot alignment errors. The ideas disclosed herein comprise collecting signals from a multitude of aperture sizes, and using the information collectively to extrapolate the data to a "no-diffraction limit" where the metrology performance is clean of the contaminating interference effects.

Figure 7:
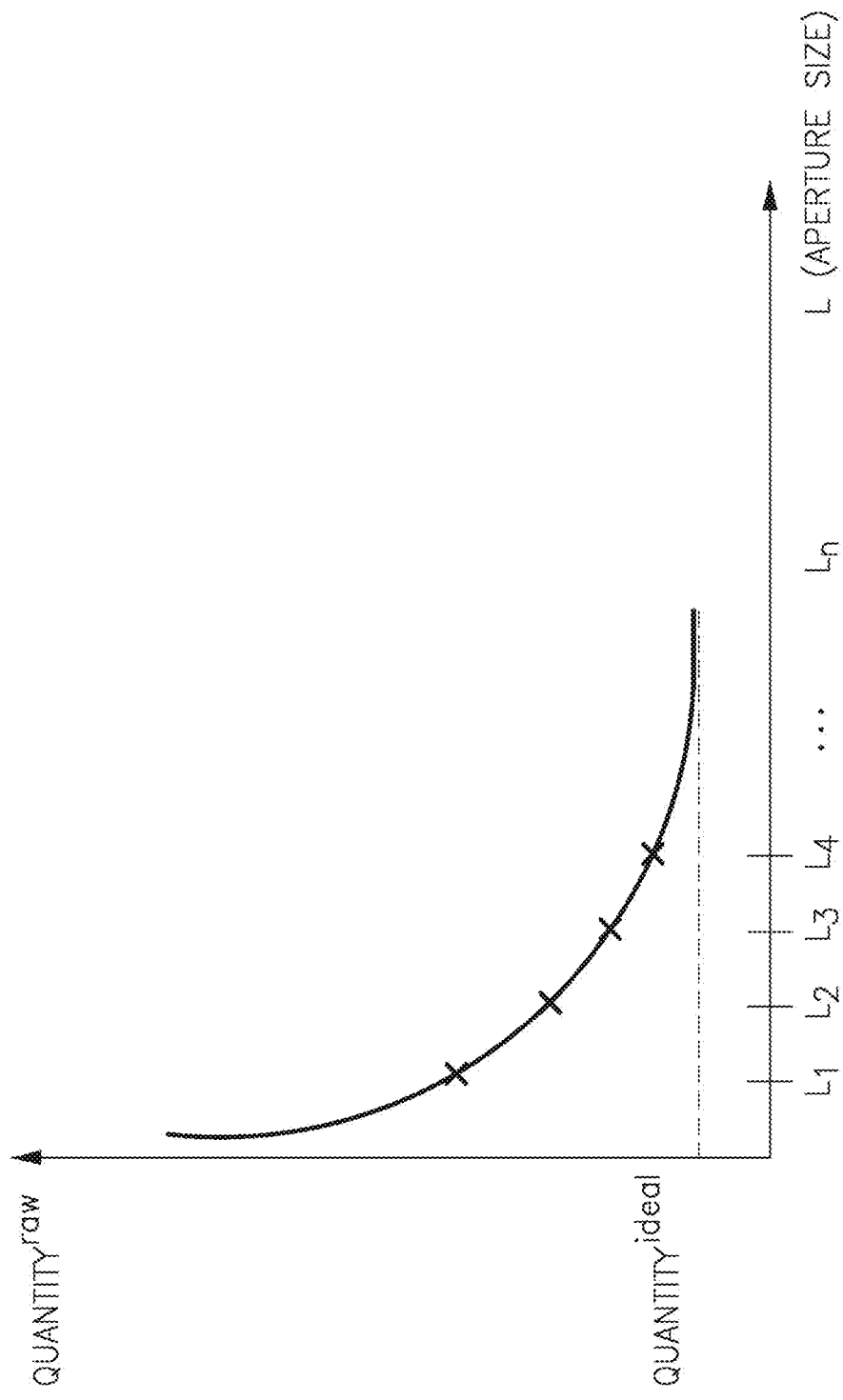
FIG. 7 is a high level schematic illustration of a generic dependency of some measurable variable termed "Quantityraw" on an aperture size in the system, according to some embodiments of the invention.

This idea is illustrated schematically in FIG. 7, illustrating a generic dependency of some measurable variable termed "Quantity$^{raw}$" on an aperture size of one of an aperture in system 90, e.g. the smallest aperture. The measured raw quantity is denoted by Quantity$^{raw}$ and the aperture size is denoted by L. $L_1, L_2, L_3, \ldots, L_n$ denote the values that L obtains in measurement no. 1, 2, 3, ... n. The no-diffraction limit is obtained at L=∞ where Quantity$^{raw}$=Quantity$^{ideal}$ and a goal of the disclosed methods is to extrapolate the data collected for Quantity$^{raw}$ at L=$L_1, L_2, L_3, \ldots, L_n$ to L=∞, to obtain an estimate for Quantity$^{ideal}$, which can be used to correct Quantity$^{raw}$ measured at a given aperture size.

Because the metrology error effects induced by diffractions may behave in a fluctuating manner as a function of L, the system and method may perform a train mode to choose the values of L for which the function Quantity$^{raw}$(L) is smooth and from which the extrapolation to L→∞ can be done.

Such dependencies of measured variables on aperture sizes may be measured with respect to different apertures in system 90 to create a multiple dimensional correction matrix referring to some or all apertures in system 90. The relevant apertures for analysis may be selected according to their sizes, or according to their influence on the resulting diffraction error. For example, a first approximation may comprise compensating for diffraction effects caused by the smallest aperture. In the case of two similar smallest apertures, the correction matrix may be two dimensional.

The "Quantity" which is extrapolated to its L→∞ limit and that is plotted on the y-axis may be one or more of various possible measurement parameters, such as per-pixel intensity or a derived intensity (like the differential signal in scatterometry overlay), or the ultimate metrology outcome (like the CD of a layer, or the overlay between two layers as schematically demonstrated, e.g., in FIG. 10A below). Performing the extrapolation(s) provides an estimate for the error margin in the metrology. For example, one may perform the extrapolations by two or more extrapolation techniques (e.g. different forms for the extrapolating function, different intervals in L used in the interpolation) and compare the results. The difference between the results can serve as a good estimate for the error margin in the metrology. Embodiments of the invention may use any of several instruments, such as e.g. a wheel with a number of apertures, an adjustable iris type of aperture or electro-optical devices like an SLM (spatial light modulator) to determine and modify different aperture sizes (values of L-$L_i$).

This idea is illustrated in more detail in an example given in FIG. 10A, being a schematic diagram illustrating an example for the way the inaccuracy in a scatterometry overlay measurement may depend on the size of the collection field stop, according to some embodiments of the invention. FIG. 10A demonstrates the way an overlay measurement depends on the collection field stop size for certain collection field stop sizes L (ranging ca. 4-23 μm) that have been chosen judicially to avoid the diffraction-induced metrology error fluctuations discussed above. These results were obtained in simulations of an overlay target measured with overlay scatterometry. The simulation results were calculated for a very large overlay target printed on a resist wafer. The true overlay of the simulated stack equals 16 nm and the deviation from 16 nm is a result of a misalignment error of the illumination with respect to the overlay scatterometry target.

Figure 8:
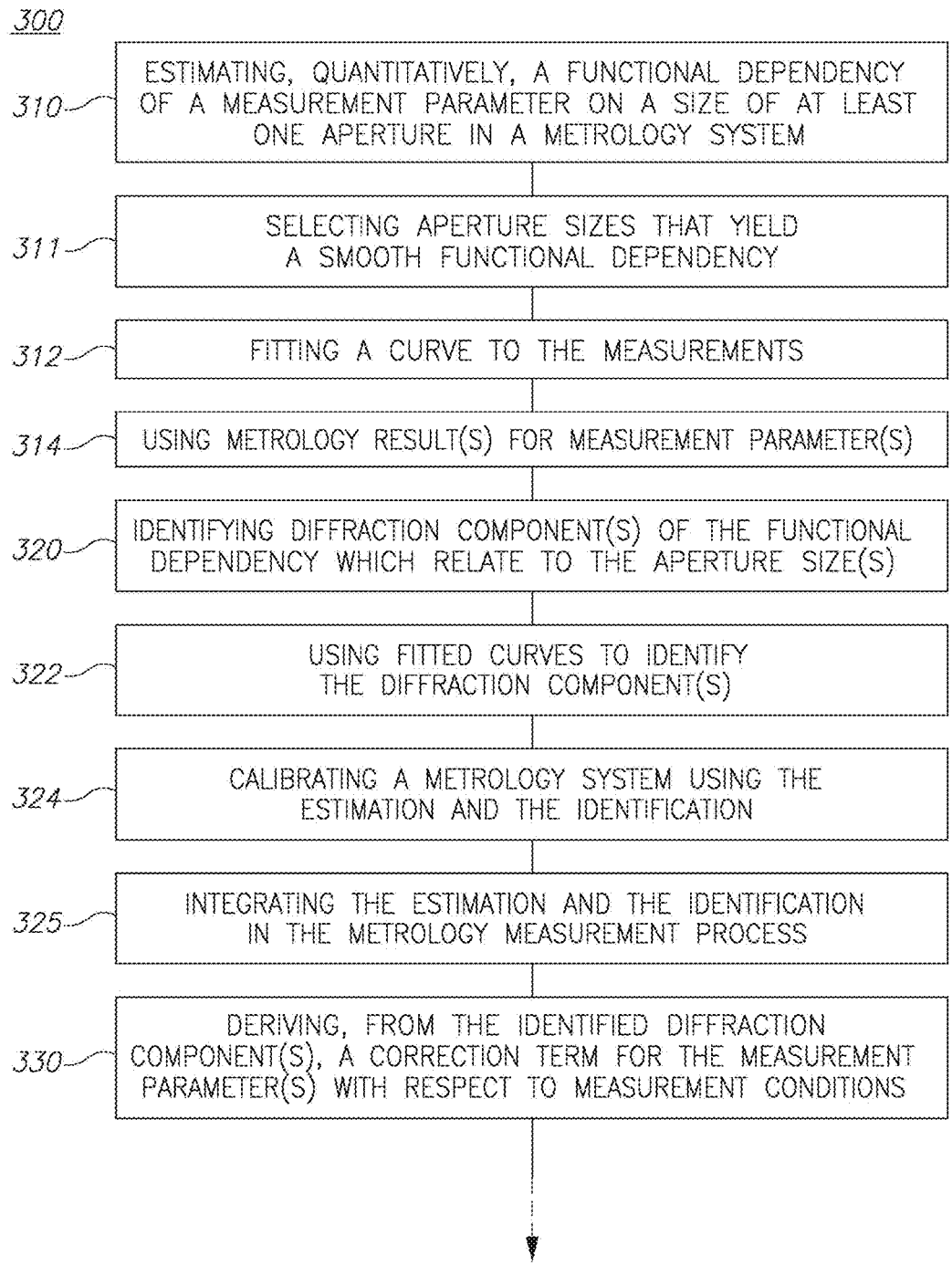
FIG. 8 is a high level schematic flowchart illustrating a method of algorithmically eliminating diffraction from optical metrology, according to some embodiments of the invention.

FIG. 8 is a high level schematic flowchart illustrating a method 300 of algorithmically eliminating diffraction from optical metrology, according to some embodiments of the invention.

Method 300 comprises estimating, quantitatively, a functional dependency of at least one measurement parameter on a size of at least one aperture in a metrology system (stage 310); identifying at least one diffraction component of the functional dependency which relates to the size of the at least one aperture (stage 320); and deriving, from the at least one identified diffraction component, at least one correction term for the at least one measurement parameter with respect to measurement conditions (stage 330). The measurement conditions comprise specified sizes of the at least one aperture that generate a diffraction error in the at least one measurement parameter. The measurement conditions may further comprise additional parameters such as illumination wavelengths and illumination source properties (e.g. spot alignment). Method 300 further comprises compensating, computationally, for the diffraction error by applying the derived correction term(s) to the at least one measurement parameter (stage 340). Thus, method 300 corrects measurement parameters by computationally removing diffraction errors due to aperture sizes (stage 342).

In an example embodiment, at least one of estimating 310, identifying 320, deriving 330 and compensating 340 may be carried out by at least one computer processor 105. In an example embodiment, a computer program product comprising a computer readable storage medium having computer readable program embodied therewith is disclosed, The computer readable program is configured to carry out at least one of stages 310, 320, 330 and 340 of method 300, as well as any other stages of method 300.

In an example embodiment, method 300 may further comprise selecting aperture sizes that yield a smooth functional dependency (stage 311). The aperture sizes may be selected to yield a functional dependency that enables identification 320 and derivation 330. In an example embodiment, the appropriate aperture sizes may be selected by going through different aperture sizes in a train mode.

In an example embodiment, estimating 310 may be carried out by fitting a curve to the measurements (stage 312) according to theoretical or analytical considerations or simulation results. Identification 320 may then be carried out by using the fitted curves to identify the diffraction component(s) (stage 322)—e.g. as terms in a series describing the fitted curve.

In an example embodiment, method 300 may comprise using at least one metrology result as the at least one measurement parameter (stage 314), e.g. the at least one metrology result may comprise any of an overlay measurement, a critical dimension (CD) measurement, a focus measurement, a dose measurement, side-all angle calculations, a film thickness measurement, etc. In an example embodiment, method 300 may comprise integrating, estimating 310, and identifying 320 in a metrology measurement process (stage 325) to continuously monitor and if necessary update the correction term(s) according to measurements carried out in the fly.

In an example embodiment, estimating 310 and identifying 320 may be carried out prior to a metrology measurement process and be used to calibrate the metrology system (stage 324). In an example embodiment, method 300 may further comprise refining the correction by reiterating the error estimation (stage 345), e.g. by calibrating metrology measurements according to the derived correction term, as explained below. In an example embodiment, method 300 may comprise deriving a second order correction term by reiterating any of estimating 310, identifying 320 and deriving 330 after a first order compensating 340.

Figure 9:
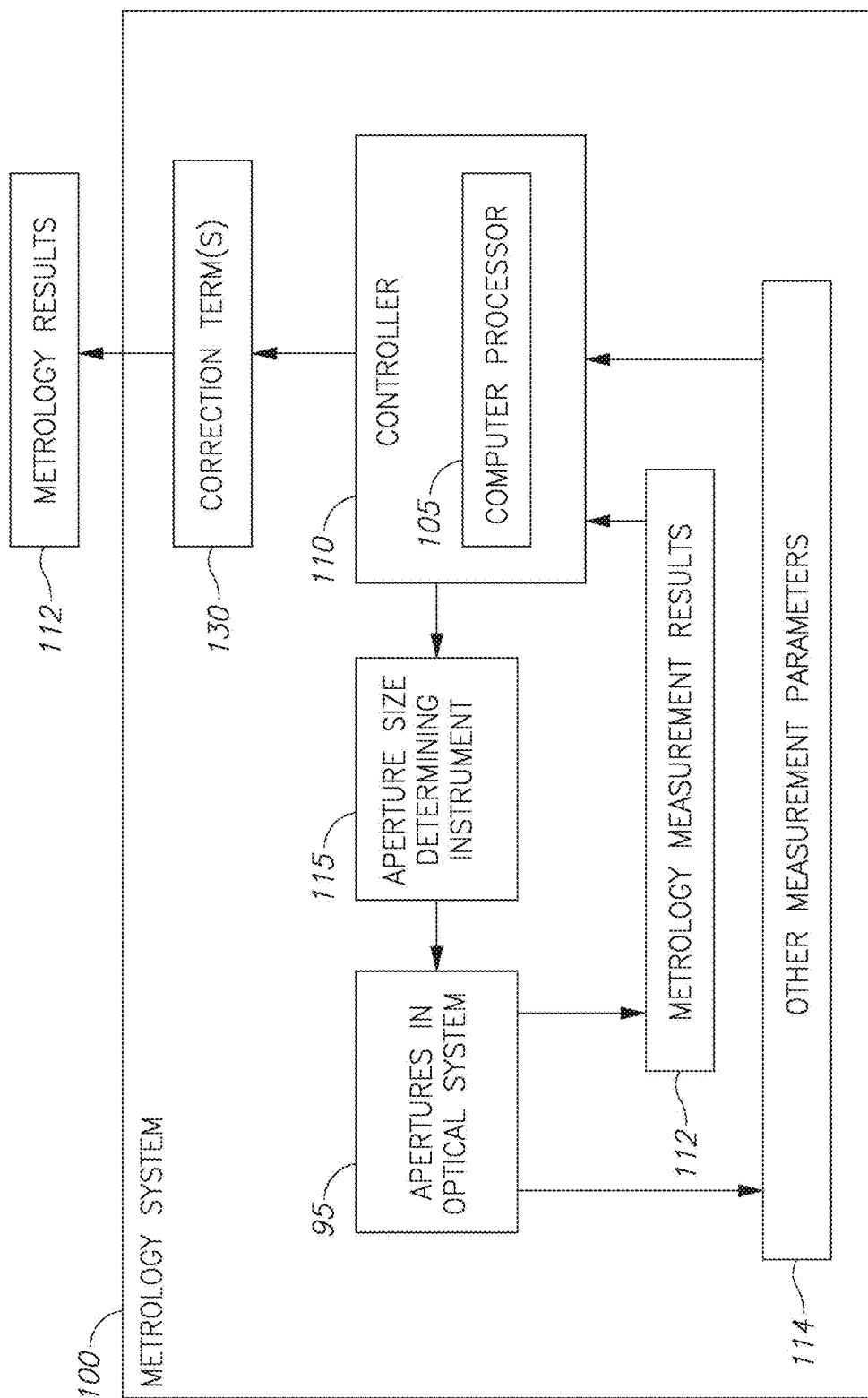
FIG. 9 is a high level schematic block diagram illustrating a metrology system, according to some embodiments of the invention.

FIG. 9 is a high level schematic block diagram illustrating a metrology system 100, according to some embodiments of the invention.

Metrology system 100 is arranged to compensate computationally for a diffraction error associated with a size of at least one aperture 95 in metrology system 100 by applying one or more correction terms 130 to at least one measurement parameter 114. The measurement parameters 114 may comprise either metrology measurement results 112 such as the critical dimension (CD) of a layer or an overlay between two layers and/or other measurement parameters 114 such as a per-pixel intensity or a derived intensity (like the differential signal in scatterometry overlay). Correction term(s) 130 may be derived by estimating, quantitatively, a functional dependency (e.g. FIGS. 7, 10A) of the measurement parameter(s) 114 on the size of aperture 95 and identifying at least one diffraction component of the functional dependency which relates to the size of aperture 95. Metrology system 100 may comprise a controller 110 (e.g. having at least one computer processor 105) arranged to carry out the estimating and the identifying (e.g. by controlling aperture size and measuring parameters) on the fly and/or arranged to, calibrate metrology system 100 according to the identifying at least one diffraction component of the functional dependency. The actual manipulation of aperture size may be carried out by any aperture size determining instrument 115 such as e.g. a wheel with a number of apertures 95, an adjustable iris type of aperture 95, or electro-optical devices like an SLM.

In an example embodiment, the estimation of the functional dependency may be carried out with respect to a selected plurality of aperture sizes which yield such functional dependency that enables the identification and the derivation (e.g. by being a smooth function).

In an example embodiment, correction terms 130 for several apertures 95 may be calculated dependently or independently to create a multiple dimensional correction matrix referring to some or all apertures in system 100.

In an example embodiment, system 100 may be further arranged to refine the computational compensation by using the functional dependency to derive a second order correction term and adjust the at least one measurement parameter 114 accordingly. In an example embodiment, system 100 may be arranged to reiterate the correction process to compensate for different errors to sequentially refine the results and reduce the measurement errors.

In an example embodiment, estimation (stage 210) may comprise fitting a curve (based e.g. on theoretical, analytical or simulation results) for the functional dependency of Quantity$^{raw}$ on the aperture size L as L→∞. The fitting parameters may then be used to calculate Quantity$^{ideal}$. For example, if the function dependency is expressed (Equation (1)): Quantity$^{raw}$(L)=A+Correction(L), where Correction(L)=B/L$^{q1}$+C/L$^{q2}$+D/L$^{q3}$+ . . . , where 0<$q_1$<$q_2$<$q_3$<. . . , then the ultimate metrology result would be A because Quantity$^{ideal}$≡Quantity$^{raw}$(L→∞)=A. In that case, compensating (stage 240) may comprise simply replacing the metrology measurements Quantity$^{raw}$(L) by the fit parameter "A", thereby extrapolating Quantity$^{raw}$(L) to its L∞→ "no-diffractions" limit. This procedure requires the measurement of Quantity$^{raw}$(L) at least for two values of L, which are judicially chosen as explained above (FIG. 7).

In cases where the function Correction(L), and equivalently, the coefficients B, C, D, . . . , exhibit an approximate universal dependency on the system parameters (which means they depend much more strongly on the wavelength, polarization, illumination profile, etc., than on the wafer metrology like the overlay and the deviation of the CD from the nominal CD), the following estimation procedure may be used.

One would first determine the function Correction(L), or equivalently the coefficients B, C, D, . . . , which define it. These coefficients may be accurately fixed in train mode (by using a large multitude of L-values, and by an increased light level/measurement time). This fixes the functional dependency of Quantity$^{raw}$(L) on L and allows one to correct Quantity$^{raw}$(L) on-the-fly and to arrive at an accurate estimate of Quantity$^{ideal}$, by using one measurement of Quantity$^{raw}$(L) at a single value of L. For example, if one performs a train measurement and finds that to a good approximation, C, D, . . . , are all negligible, but that B is a non-negligible function of tool-only parameters then one may correct for the metrology outcome by replacing it, at a given value of L, in the following way (Equation (2)): Metrology outcome=Quantity$^{raw}$(L)→Metrology outcome=Quantity$^{raw}$(L)−B/L$^{q1}$. That is, the systems and methods may identify non-negligible terms of the correction function and their type of dependency on the system parameters, and correct measurements only by these non-negligible terms, in respect of their dependencies on system parameters.

It is noted in passing that the afore-mentioned assumption on the universal behavior of the function "Correction(L)" is a very reasonable one and is supported by simulations (see below) as the metrology outcome affects the diffractions very weakly (such as the overlay or the deviation of the CD value from the nominal CD). For example the overlay enters into the diffraction effect in a functional form which depends on the combination 2π·overlap/Pitch. As the pitch is around 600 nm, the error induced by this dependency is in the order of a few percent.

Advantageously, the current invention improves measurement accuracy by suppressing the aperture induced diffraction effects. In addition to establishing Quantity$^{ideal}$, it provides a way of calculating the margin of error (Quantity$^{raw}$−Quantity$^{ideal}$), since that is one of the outcomes of the fitting procedures done in measurement or in train mode. This provides a quantitative confidence in the measurements.

FIG. 10A is a schematic diagram illustrating an example for the way the inaccuracy in a scatterometry overlay measurement may depend on the size of the collection field stop, according to some embodiments of the invention. FIG. 10A is used in the following as a detailed non-limiting example of the way the current invention may be applied to overlay metrology. In this illustrated case, the "Quantity" is the overlay reported by overlay scatterometry, the "L"s are the collection field stop sizes, and the error in the overlay estimation is due to a misalignment between the illumination spot and the grating structure that is being measured.

FIG. 10B is a schematic diagram illustrating an example for the way the inaccuracy in a scatterometry overlay measurement depends on the size of the collection field stop for two different values of the true overlay, according to some embodiments of the invention. As FIG. 10B clearly shows, this error decreases to zero when L increases (the simulated overlay was chosen to be 16 nm in this example, as illustrated in FIG. 10A). The values of L chosen for the plot were chosen according to the description above. FIG. 10B also clearly demonstrates that the dependence of the inaccuracy on the metrology parameters (the overlay in the current example) is negligible as the 'universality' assumption stated above declares.

In the current example, implementing method 300 may comprise the following stages. First, stage 312 comprises fitting the data in FIG. 10A: A very good fit is found to a function of the form: $OVL(L)=A+18.885/L^p$, which describes the simulation data well for $p \approx 2.0$ and $A=16.027$. The final metrology overlay results are then the value $OVL(L \rightarrow \infty)=A=16.027$. This would lead to an overlay error inaccuracy of 0.027 nm (recalling that the true overlay used in these exemplary simulations is 16 nm). Stage 314 comprises using the calculated inaccuracy to correct the measurements.

Advantageously, the fit can also be done from the lower two stop size values of $L=4.15$ μm and $L=7.25$ μm only. In such case the value of A becomes 16.215, leading to an inaccuracy estimation of 0.215 nm (using $L=7.25$ μm alone gives an inaccuracy of around ~0.5 nm and the result of $L=4.15$ μm gives an inaccuracy of around ~1.1 nm).

Another way of implementing method 300 is to consider the fit discussed above as a calibration to the way overlay values depend on the collection field stop size. To demonstrate this fact, FIG. 10B further shows how the overlay inaccuracy behaves for two overlay targets, whose overlay values equal 0 nm and 16 nm. As clearly illustrated by FIG. 10B, the inaccuracy depends only very weakly on the true overlay of the stack, as argued above. This opens the way to perform the following type of second order calibration (stage 324), namely (i) using the calibration formula obtained by fitting the overlay data (in the example above this formula is $OVL(L)=16.027+18.885/L^2$), and then (ii) applying the formula to a new overlay measurement in the following way (the new overlay measurement are denoted by OVL'(L)). First, the new overlay measurement OVL'(L) is replaced by a corrected measurement: $OVL'(L)=OVL'(corrected,L)=OVL'(L)-18.885/L^2$.

Figure 11A:
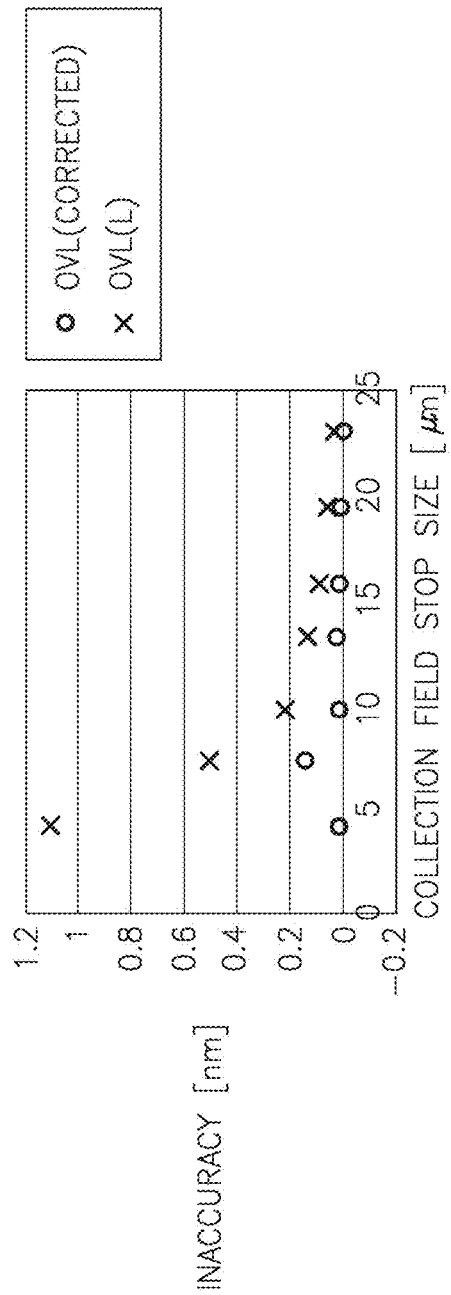
FIG. 11A is a schematic diagram illustrating an example for the way the correction method using a first type of calibration reduces the overlay measurement error, according to some embodiments of the invention.

FIG. 11A is a schematic diagram illustrating an example for the way the correction method using a first type of calibration reduces the overlay measurement error, according to some embodiments of the invention. FIG. 11A illustrates the improvement achieved by applying the second order approximation as described above. In the illustrated example, the resulting error reduction by the calibration is presented for a case where the true overlay=0. Note that this involves a single measurement at a single value of L.

Clearly, the uncalibrated results lead to significant overlay errors, especially for small collection field stop sizes, while the calibrated results reduce these errors significantly. Note that these errors can also cause precision degradation if the root cause for the inaccuracy (spot misalignment in the current example) fluctuates in time.

Figure 11B:
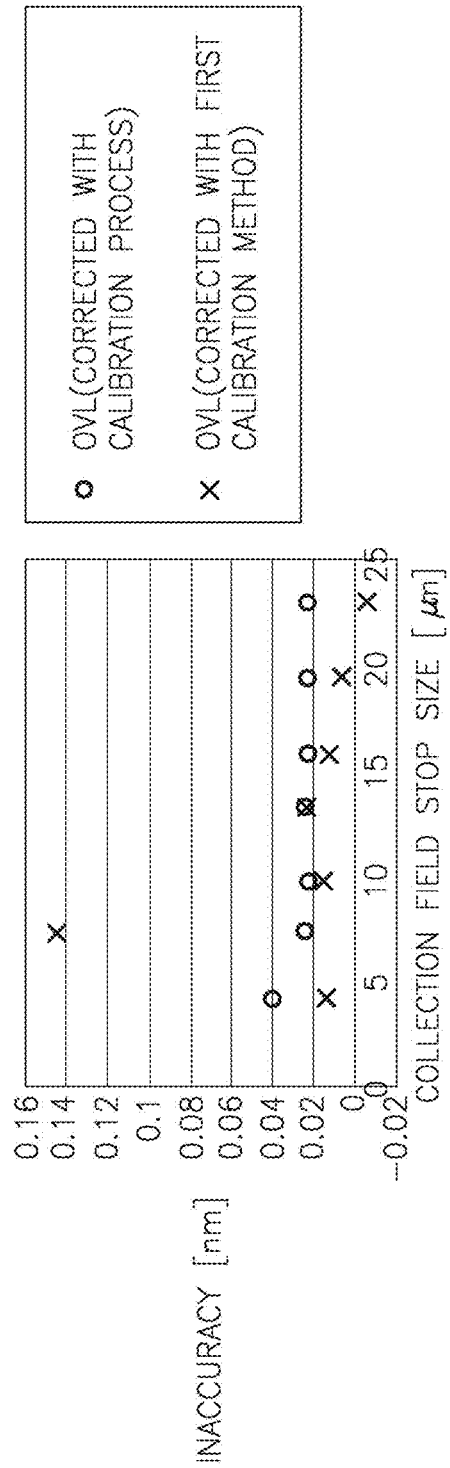
FIG. 11B is a schematic diagram illustrating an example for the way the correction method using a second type of calibration reduces the overlay measurement error, according to some embodiments of the invention.

FIG. 11B is a schematic diagram illustrating an example for the way the correction method using a second type of calibration reduces the overlay measurement error, according to some embodiments of the invention. The second type of calibration is carried out in the following manner. First, the overlay measurements that were used for calibration are denoted by by OVL(L;0). For example, these may be the measurements which were fitted to $OVL(L;0)=A+Correction(L)$, where $A=16.027$, and $Correction(L)=18.885/L^2$. At this point, the best estimate for the true overlay in this calibration measurement is 16.027 nm. In this second type of calibration, the fact that the diffraction effects on the two overlay measurements depend very weakly on the actual value of the overlay, is used to correct the new overlay measurement. The new overlay measurement is denoted by OVL(L;1) as follows: $OVL(L;1) \rightarrow OVL(L;1,corrected)=OVL(L;1)+OVL(L;0)-A$. As illustrated in FIG. 11B, the second type of calibration is preferable, in this example, to the first type of calibration as it yields more stable corrections with respect to a varying stop size.

It is noted in passing that in both calibration methods presented above, it is important that the measurement conditions do not changed significantly from the calibration measurement to the actual measurement. This includes the light properties (wave-length, polarization, alignment of system with respect to target, focus, etc.). In case it cannot be assured that the measurement conditions are the same, additional calibrations may be needed to calibrate and compensate for the differences. For example, if an overlay scatterometry system is misaligned along the x-axis by an amount d with respect to a large overlay target, then the overlay measurement, OVL, should be formulated as a two dimensional function which depends on the collection field stop size, L and on d: OVL(L,d). Since at $L \rightarrow \infty$, the decentering causes zero inaccuracy the function may be expressed as $OVL(L,d)=A+f(d) \cdot g(L)$, with $g(L \rightarrow \infty)=0$.

In the two dimensional case, the calibration process may be divided into the following steps. First, d may be fixed at a $d_0$ and $OVL(L, d_0)$ is fitted to obtain A. The Correction (d,L) is defined as $Correction(d,L) \equiv OVL(L,d)-A$, and the $Correction(d_0,L)=f(d_0) \cdot g(L)$ is obtained. Then, the Correction($d_0$,L) is divided by Correction ($d_0,L_0$) to obtain a numerical estimate for the ratio $r_g(L)=g(L)/g(L_0)$.

These steps are then repeated for various values of $d_i=d_1$, $d_2$, $d_3$, $d_4$, etc. to obtain Corrections ($d_i$, L) and, by dividing these results as explained above—Correction($d_i$,L)/Correction($d_i,L_i$), the numerical estimates for function $r_f(d)=f(d)/f(d_0)$ are formed. Combining the above steps and the measurement of the overlay at $L=L_0$ and $d=d_0$, which provides Correction($L_0,d_0$), the numerical estimate for OVL(L,d) can be expressed as $OVL(L,d)=A+Correction(L_0,d_0) \cdot r_f(L) \cdot r_g(d)$. As a result, for any new overlay measurement OVL(L, d) performed at some values of L and d, the correction would be $OVL(L,d) \rightarrow OVL(L,d;corrected)=(OVL(L,d)-Correction(d_0,L_0) \cdot r_g(L) \cdot r_f(d)$.

Method 300 may thus further comprise calibrating the correction term with respect to at least one difference between derivation conditions (of metrology system 100 during the derivation) and measurement conditions (stage 332). The at least one difference may relate, for example, to the wavelength or polarization of the measurement beam, to alignment of system 100 with respect to a target, to focus parameters, etc.

In an example embodiment, method 300 further comprises carrying out calibration 332 by expressing the functional dependency as relating to the at least one difference (stage 334) and deriving the correction term with further respect to a range of values of the at least one difference (stage 336).

Respectively, in an example embodiment, metrology system 100 may be further arranged to calibrate the correction term with respect to at least one difference between derivation conditions and measurement conditions, wherein the at least one difference relates to at least one of: wavelength, polarization, alignment with respect to a target, and focus. Metrology system 100 may be arranged to carry out the calibration by expressing the functional dependency as relating to the at least one difference and deriving the correction term with further respect to a range of values of the at least one difference.

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Embodiments of the invention may include features from different embodiments disclosed above, and embodiments may incorporate elements from other embodiments disclosed above. The disclosure of elements of the invention in the context of a specific embodiment is not to be taken as limiting their use in the specific embodiment alone.

Furthermore, it is to be understood that the invention can be carried out or practiced in various ways and that the invention can be implemented in an example embodiment other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. An angle-resolved reflectometer comprising:
   a coherent illumination source;
   a controller, wherein the controller includes one or more processing units;
   an optical system arranged to scan a test pattern of a sample with a spot of coherent light from the coherent illumination source, wherein the scan is configured with an adjustable scan size and density, wherein the scan is performed according to a scanning pattern, wherein the scanning pattern causes the spot to be scanned across the test pattern, wherein the optical system includes a scanning mirror configured to control a position of the spot of coherent light;
   a detector configured to collect light reflected from the test pattern of the sample to yield a plurality of pupil images of a light distribution in a collection pupil; and
   a processing unit configured to generate a composite image by combining two or more of the plurality of pupil images of the light distribution collected in the collection pupil.

2. The angle-resolved reflectometer of claim 1, wherein the scanning mirror is configured to position the spot of coherent light on the sample during an overlay measurement.

3. The angle-resolved reflectometer of claim 1, wherein the processing unit is further configured to control the scanning mirror.

4. The angle-resolved reflectometer of claim 3, wherein the processing unit is further configured to modify the light distribution and identify an optimal intensity distribution with respect to a specific test pattern or metrology configuration.

5. The angle-resolved reflectometer of claim 1, wherein the processing unit is further configured to identify high-noise regions of the test pattern.

6. The angle-resolved reflectometer of claim 5, wherein the processing unit is configured to remove the identified high-noise regions of the test pattern from the scanning pattern.

7. The angle-resolved reflectometer of claim 1, wherein the processing unit is further configured to identify high-noise regions of the test pattern in an optical scan.

8. The angle-resolved reflectometer of claim 7, wherein the processing unit is configured to avoid the identified high-noise regions of the test pattern during the optical scan.

9. The angle-resolved reflectometer of claim 1, wherein the scanning pattern comprises a light distribution that is symmetric and non-uniform.

10. The angle-resolved reflectometer of claim 1, wherein the processing unit is further configured to reduce speckle in the composite image utilizing the plurality of pupil images of a light distribution in the collection pupil.

11. The angle-resolved reflectometer of claim 1, wherein the coherent illumination source is a laser.

12. An angle-resolved reflectometry method comprising:
    directing a spot of coherent light, with a scanning mirror, to a test pattern, wherein the spot of coherent light is smaller than a size of the test pattern;
    scanning, with the scanning mirror, the test pattern with the spot of coherent light to yield a plurality of pupil images of a light distribution in a collection pupil, wherein the scanning is carried out according to a scanning pattern that causes the spot to be scanned across the test pattern, wherein the scanning pattern scan size and scan density are adjustable;
    collecting, with a detector, light reflected from the test pattern to yield a plurality of test pattern images; and
    generating, with one or more processing units, a composite image of collected pupil light distribution by combining two or more of the plurality of pupil images of the light distribution in the collection pupil.

13. The angle-resolved reflectometry method of claim 12, further comprising:
    positioning, with the scanning mirror, the spot of coherent light on a sample during an overlay measurement.

14. The angle-resolved reflectometry method of claim 12, further comprising:
    identifying high-noise regions of the test pattern; and
    removing the identified high-noise regions of the test pattern from the scanning pattern.

15. The angle-resolved reflectometry method of claim 12, further comprising:
    identifying high-noise regions in an optical scan; and
    avoiding the identified high-noise regions of the test pattern during the optical scan.

16. The angle-resolved reflectometry method of claim 12, wherein the scanning pattern comprises a specified intensity distribution.

17. The angle-resolved reflectometry method of claim 12 further comprising:
    scanning the test pattern utilizing the one or more processing units to control a configuration of the scanning mirror.

18. The angle-resolved reflectometry method of claim 12, further comprising:
    reducing speckle in the composite image utilizing the plurality of pupil images of the light distribution collected in the collection pupil from a stationary spot position.

19. The angle-resolved reflectometry method of claim 12, further comprising:

scanning the test pattern utilizing a scanning pattern that includes a light distribution that is symmetric and non-uniform.

20. The angle-resolved reflectometry method of claim 12 further comprising:

modifying the light distribution and identifying an optimal intensity distribution with respect to a specific test pattern or metrology configuration.

* * * * *